(12) United States Patent
Laurila et al.

(10) Patent No.: US 9,708,609 B2
(45) Date of Patent: Jul. 18, 2017

(54) METHODS TO SCREEN COMPOUNDS FOR REGULATING USF1 ACTIVITY AND METHODS AND COMPOUNDS TO TREAT CARDIOMETABOLIC AND LIPID PATHOLOGIES

(71) Applicant: Terveyden ja hyvinvoinnin laitos (THL), Helsinki (FI)

(72) Inventors: Pirkka-Pekka Laurila, Helsinki (FI); Jarkko Soronen, Helsinki (FI); Matti Jauhiainen, Helsinki (FI); Anu Jalanko, Helsinki (FI)

(73) Assignee: Terveyden ja hyvinvoinnin laitos (THL), Helsinki (FI)

( * ) Notice: Subject to any disclaimer, the term of this patent is extended or adjusted under 35 U.S.C. 154(b) by 0 days.

(21) Appl. No.: 14/746,281

(22) Filed: Jun. 22, 2015

(65) Prior Publication Data

US 2015/0368641 A1    Dec. 24, 2015

Related U.S. Application Data

(60) Provisional application No. 62/014,730, filed on Jun. 20, 2014.

(51) Int. Cl.
*C12N 15/11* (2006.01)
*C12N 15/113* (2010.01)
*G01N 33/50* (2006.01)

(52) U.S. Cl.
CPC .......... *C12N 15/113* (2013.01); *G01N 33/502* (2013.01); *G01N 33/5088* (2013.01); *C12N 2310/11* (2013.01); *C12N 2310/14* (2013.01); *G01N 2333/4703* (2013.01)

(58) Field of Classification Search
CPC ............................ C12N 15/111; C12N 15/113
See application file for complete search history.

(56) References Cited

U.S. PATENT DOCUMENTS

2008/0050358 A1 * 2/2008 Peltonen-Palotie ............... C07K 14/4705
424/130.1

OTHER PUBLICATIONS

Sirito et al. (PNAS 1998, vol. 95, pp. 3758-3763).*
Laurila et al. (Science Translational Medicine (Jan. 2016), vol. 8, 21 pages).*
Avery et al. (Molecular Pharm. (2013) 85:1-10).*
Yuyama et al. (Biochem. Journal (2014) 459(3):489-503).*

* cited by examiner

*Primary Examiner* — Jon E Angell
(74) *Attorney, Agent, or Firm* — Berggren, Inc.

(57) ABSTRACT

The deficiency of Usf1 confers a remarkable number of clinically relevant beneficial metabolic effects in mice via activation of brown adipose tissue. The Usf1 deficient mice have high serum HDL-cholesterol and low triglyceride levels, a beneficial lipid profile opposite to that of human metabolic syndrome. The elevated HDL-C is associated with enhanced cholesterol efflux, and low triglycerides with decreased hepatic VLDL production and elevated triglyceride clearance. Despite their elevated food intake and lower physical activity, the Usf1 deficient mice are protected against diet-induced obesity. Their concomitant increase in energy expenditure is related to the activation of brown adipose tissue. The protective effects of Usf1 deficiency against obesity, insulin resistance, fatty liver, dyslipidemia, vascular inflammation, and atherosclerosis coupled with brown adipose tissue activation are demonstrated. Inhibition or silencing of USF1 is suggested as a therapeutic target to treat various human diseases.

10 Claims, 20 Drawing Sheets

A)

B)

C)

METHODS TO SCREEN COMPOUNDS FOR REGULATING USF1 ACTIVITY AND METHODS AND COMPOUNDS TO TREAT CARDIOMETABOLIC AND LIPID PATHOLOGIES

PRIORITY

This application claims the priority of U.S. Ser. No. 62/014,730 filed on Jun. 20, 2014 the contents of which are fully incorporated herein by reference.

SEQUENCE LISTING

This application contains sequence data provided on a computer readable format and as a paper version. The paper version of the sequence data is identical to the computer readable format.

FIELD OF THE INVENTION

The invention relates to methods and compounds to treat cardometabolic and lipid pathologies as well as to methods to screen such compounds.

BACKGROUND OF THE INVENTION

Usf1 (Upstream stimulatory factor 1) is a helix-loop-helix leucine zipper family transcription factor[1] which in early reports was demonstrated to be part of the general transcription machinery of the cell[2,3]. The role of Usf1 in lipid metabolism was established in our laboratory when we first identified region 1q21-23 to be linked to familial combined hyperlipidemia (FCHL) in Finnish families[4], and then pinpointed Usf1 to be the causative gene[5]. The clinical relevance of Usf1 in humans has further been established for coronary atherosclerosis[6,7], acute cardiovascular events[8], metabolic derangements[9], and all-cause mortality[8]. Whether the effects of Usf1 protein are beneficial or detrimental to metabolic health, and which biological processes are regulated by Usf1 has yet remained elusive.

WO2005077974 discloses SNPs of Usf1 associated with hyperlipidemia, dyslipidemia and defective carbohydrate metabolism. The publication also suggests inhibitors specific for Usf1 for treatment of hyperlipidemias and/or dyslipidemias including familial combined hyperlipidemia (FCHL), hypercholesterolemia, hypertriglyceridemia, hypoalphalipoproteinemia, hyperapobetaliporoteinemia, familial dyslipidemic hypertension (FDH), metabolic syndrome, type 2 diabetes mellitus, coronary heart disease, atherosclerosis or hypertension. The publication however, does not indicate how inhibitors could be used for same purpose and the publication does not disclose what the mode of action could be.

Laurila et al 2011 disclosed a congenic strain of Usf1 knockout mice showing lower plasma total VLDL TG as compared to wild type mice. The knockout mice were shown to have increased lipolysis due to higher activity of post-heparin plasma lipoprotein lipase.

Accordingly, even if there are some indications of activation or inhibition of Usf1 for treatment of hyper- and dyslipidemias, the mode of action has not been solved and accordingly no practical solutions have not been provided.

SUMMARY OF THE INVENTION

This disclosure provides results showing the master role of Usf1 in activation and control of brown adipose tissue and its numerous effects on the lipid metabolism of mammals.

In this study we demonstrate that the deficiency of Usf1 confers a remarkable number of clinically relevant beneficial metabolic effects in mice through activation of brown adipose tissue. The Usf1 deficient mice have high serum HDL-cholesterol and low triglyceride levels, a beneficial lipid profile opposite to that of human metabolic syndrome. The elevated HDL-C is associated with enhanced cholesterol efflux, and low triglycerides with decreased hepatic VLDL production and elevated triglyceride clearance. Despite their elevated food intake and lower physical activity, the Usf1 deficient mice are protected against diet-induced obesity. Their concomitant increase in energy expenditure is related to the activation of brown adipose tissue (BAT) which more effectively clears triglyceride-rich lipoproteins (TRL) from the circulation via a lipoprotein-lipase dependent mechanism. Our study, demonstrating the protective effects of Usf1 deficiency against obesity, insulin resistance, fatty liver, dyslipidemia, vascular inflammation, and atherosclerosis coupled with brown adipose tissue activation and the established role of the gene in human metabolic and cardiovascular disease, makes Usf1 appear a particularly attractive therapeutic target. The therapeutic applications according to this invention include inhibiting or silencing Usf1 on a gene transcription or protein level. Molecules and compounds capable of inhibiting or silencing the gene or protein are beneficial and useful for treating atherosclerosis, and obesity, protection against fatty liver, improving sensitivity to insulin, improving lipid profile in individual's blood and activating brown adipose tissue. The invention also includes Usf1-inhibitors that are identified either by applying the state-of-the art RNA interference technology in which the messenger RNA of Usf1 is degraded, thereby reducing the intracellular protein levels of the gene or by applying a chemical library of approximately 75,000 compounds and establishing a cell culture monitoring. We use fibroblast in both methods. To assess inhibition of the physiological function of Usf1 as a transcription factor, the expression of relevant target genes of Usf1 is measured. After finding a relevant inhibitor molecule it will be tested in vivo using a mouse model.

It is an object of this invention to provide pharmaceutically active compounds either in a form of chemical inhibitors against the Usf1 protein or antisense oligonucleotide (ASO) or siRNA approach to treat atherosclerosis, and obesity, to protect against fatty liver development, improve insulin sensitivity, enhance anti-atherosclerotic lipid profile in circulation, and induce the function of brown adipose tissue to burn triglycerides, fatty acids and glucose.

Another object of this invention is to provide an in vitro system to screen compounds capable of inhibiting or silencing Usf1 expression for use to treat atherosclerosis, and obesity, protecting against fatty liver, improve sensitivity to insulin, improve lipid profile in individual's blood and activate brown adipose tissue.

A further object of this invention is a vaccine for treating atherosclerosis, and obesity, protecting against fatty liver, improving sensitivity to insulin, improving lipid profile in individual's blood and activating brown adipose tissue.

Still another object of this invention is to increase uptake of triglycerides, fatty acids and glucose by using targeted inhibition or silencing the expression of Usf1 encoding gene in brown adipose tissue cells and/or in white adipose tissue.

An object of this invention is also to generate novel antibodies either monoclonals or polyclonals and establish an ELISA-kit using the antibodies for detection of the USF1-protein in cellular samples.

Another object of this invention is to provide a method to activate the brown adipose tissue for treating artherosclerosis, obesity, fatty liver, decreased sensitivity to insulin.

Another object of this invention is to provide a Usf1 inhibiting molecules in nanoparticles for delivery to cells in brown adipose tissue to treat.

Still another object of this invention is to provide siRNA and antisense oligonucleotide molecules to inhibit or silence USF-1 expression for activating the brown adipose tissue.

One object of this invention is to provide a method to activate brown adipose tissue by inhibiting Usf1 with siRNA sequence according to SEQ ID NO:1 or SEQ ID NO:2.

DESCRIPTION OF THE INVENTION

The invention is now described by means of non-limiting Examples. The materials and methods used in the following Examples are provided after the Examples.

Figure 1:
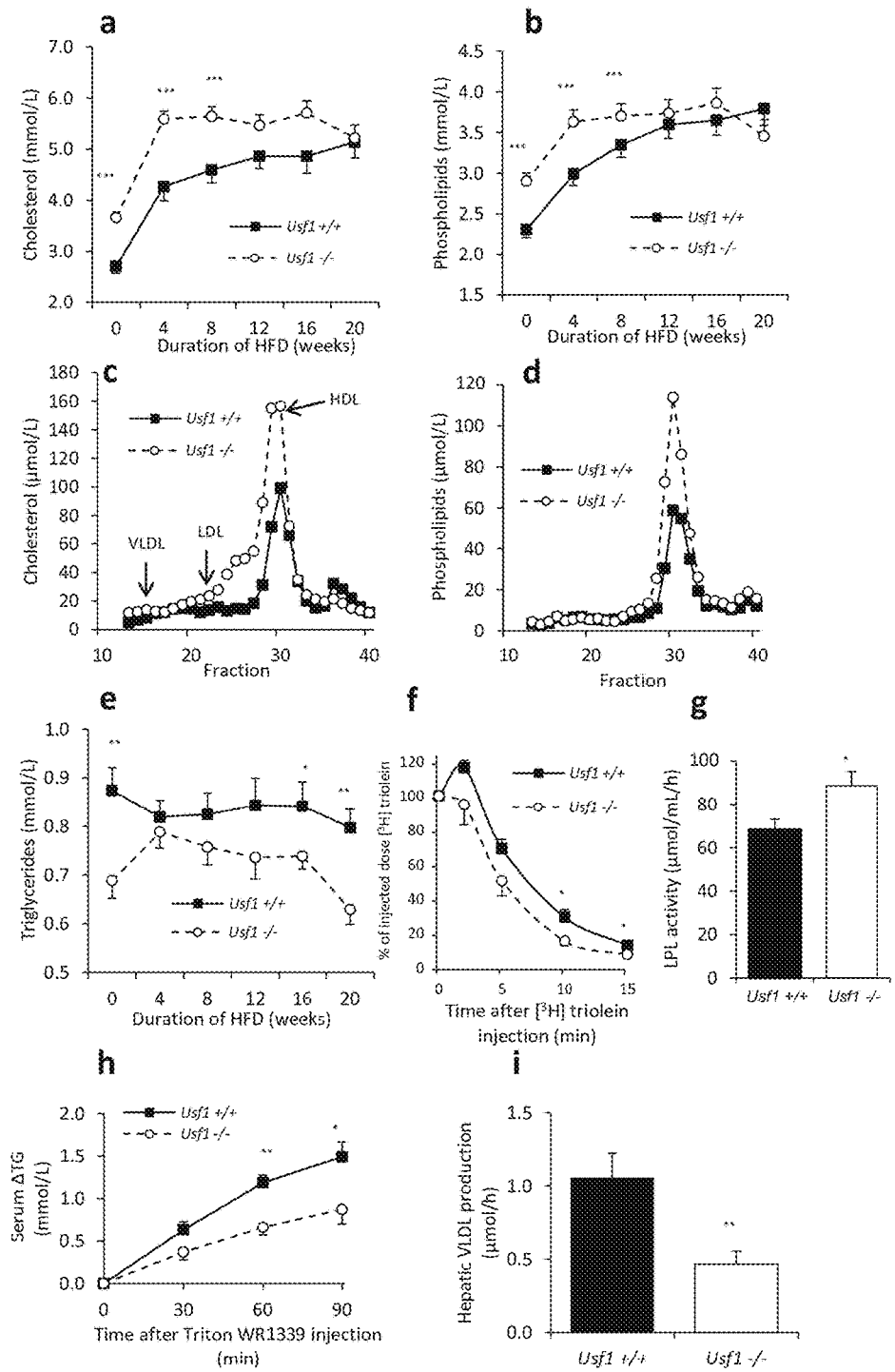
FIG. 1. Deficiency of Usf1 in mice leads to a beneficial lipoprotein profile. (a) Total cholesterol. N=23/22 (b) Phospholipid levels. N=23/22. (c) Lipoprotein analysis using FPLC shows elevated cholesterol in the HDL fractions of the Usf1 −/− mice. (d) FPLC analysis indicates that there are elevated levels of phospholipids in the HDL fractions of Usf1 −/− mice. (e) Plasma triglyceride levels. N=23/22. (f) Serum clearance of $^3$H triolein. (g) Lipoprotein lipase activity is elevated in Usf1 −/− mice after 20 weeks of HFD. N=15/14. ((h) Plasma TG concentrations after Triton WR1339 injection are plotted as the increase in plasma TG relative to t=0. N=15/9. (i) Hepatic VLDL production is reduced in chow-fed Usf1 −/− mice. The rate of TG production was calculated form the slopes of the curves from individual mice. N=15/9.0) Cholesterol efflux from THP-1 macrophages treated with non-targeting and USF1 silencing lentivirus. Sera derived from Usf1+/+ and Usf1−/− mice are used as acceptors. N=6 in each column. (k) Cholesterol efflux from THP-1 macrophages treated with non-targeting and USF1 silencing lentivirus. HDL isolated from Usf1+/+ and Usf1−/− mice are used as acceptors. N=6 in each column. (l) Mass composition (%) of HDL particles isolated from Usf1+/+ and Usf1−/− mice. N=11/9. (m) HDL particle content (mmol//L for lipid and g/L for APOA1, n=11/9. (n) APOA 1 mRNA in siRNA mediated USF1 silenced HuH7 cells compared to non targeting siRNA control (o)-(p) APOA secretion from siRNA mediated USF1 silenced HuH7 cells). All panels depict female mice. * P<0.001,  P<0.01, * P<0.05. All values are mean±s.e.m.
Figure 1:
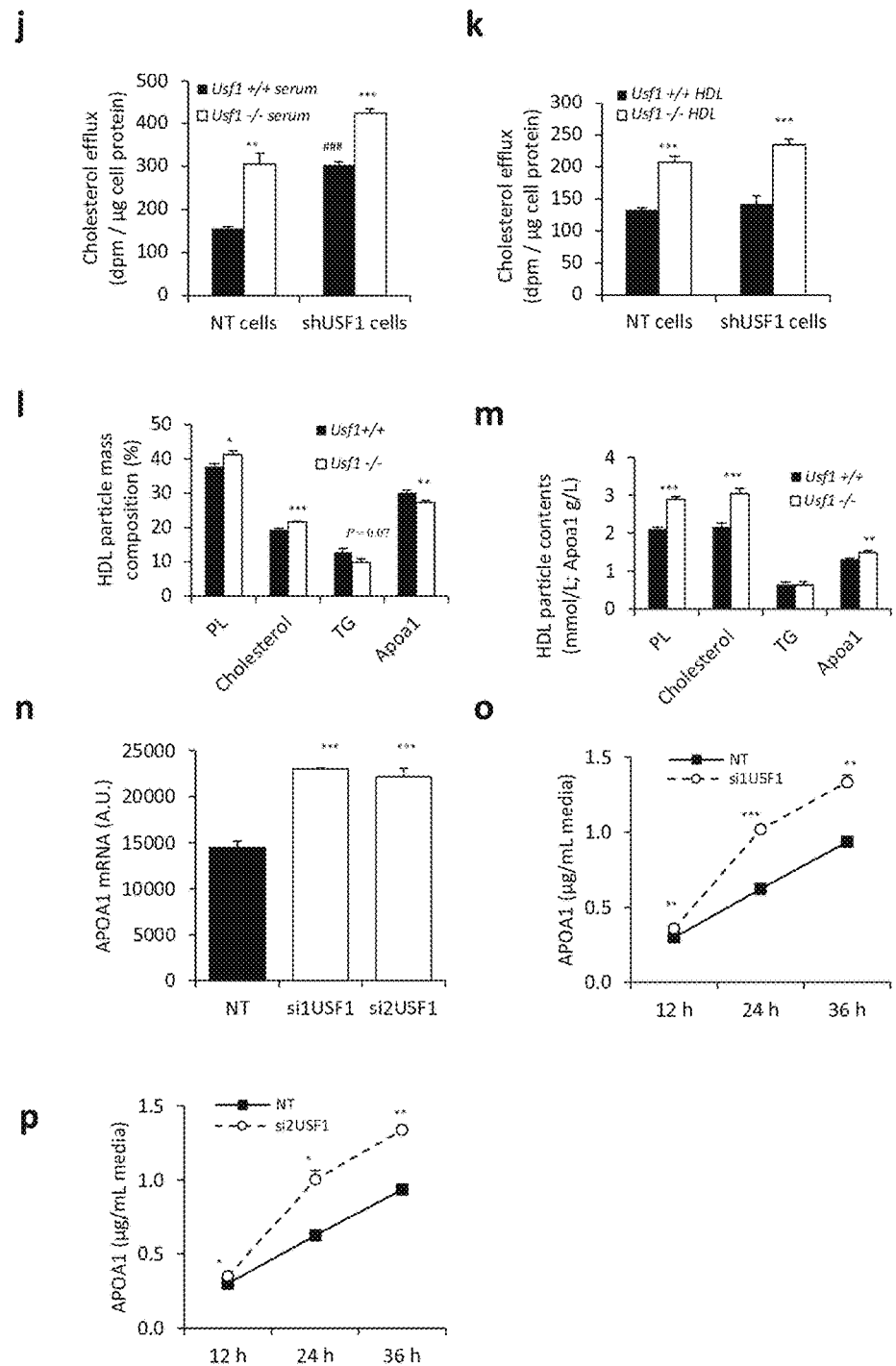

Example 1 USF-1-Deficiency or Inhibition of Usf1-Activity Affects Cholesterol Phenotype in Knockout Mice To study the effects of USF1 on lipid metabolism, we generated a mouse model deficient of Usf1 using cell lines obtained from the International Gene Trap Consortium. As USF1 is originally linked with FCHL, and its alleles in humans are associated with plasma triglyceride and HDL-C levels, we first measured the lipid profiles of the mice before and after feeding high fat diet (HFD), also known as 'Western' diet for 20 weeks. Before HFD feeding, Usf1−/− mice displayed a substantial 36% elevation in serum total cholesterol (FIG. 1a). During the HFD, the cholesterol levels increased in both Usf1+/+ and Usf1−/− mice. The Usf1−/− mice reached their maximum plateau in cholesterol levels earlier than their wild-type littermates so that at the end of the diet the genotype-related differences in plasma cholesterol had disappeared. In harmony with the cholesterol phenotype, the plasma phospholipid levels were also elevated in the Usf1−/− mice (26%) (FIG. 1c) when compared with the Usf1+/+ littermates.

Figure 5:
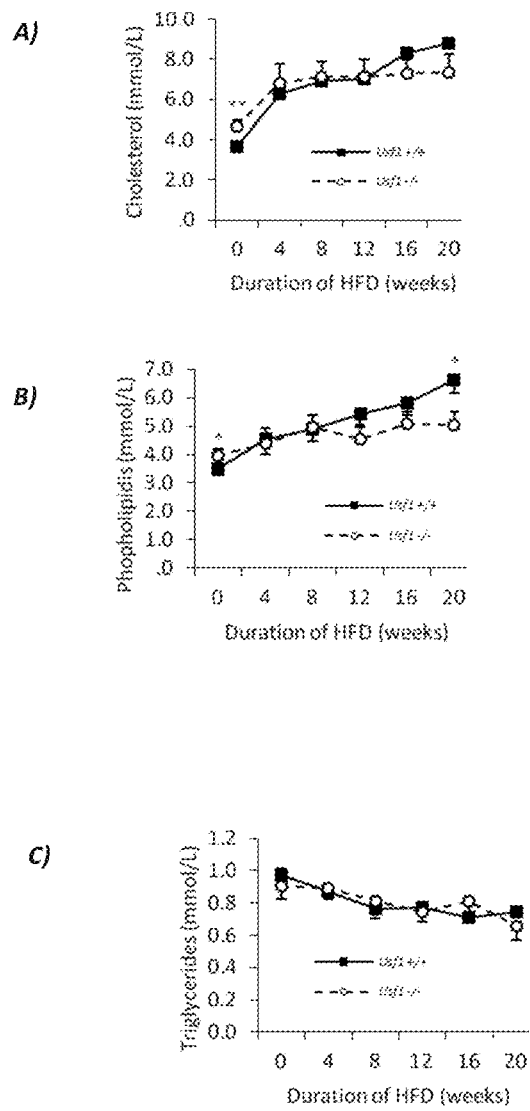
FIG. 5. Serum lipid profiles of the male Usf1 −/− mice are similar to those observed in females. Cholesterol (A), phospholipid (B) and triglyceride levels (C). N=22/7 * P<0.001,  P<0.01, * P<0.05. All values are mean±s.e.m.

We next studied which circulating lipoproteins account for the differences in plasma lipids. Both cholesterol and phospholipid levels were elevated in the HDL fractions of Usf1−/− mice, as evidenced by fast protein liquid chromatography (FPLC) (FIGS. 1b and 1d), indicating that the elevated cholesterol levels in the knockouts are likely to have a beneficial role. Moreover, the plasma triglyceride levels of Usf1−/− mice were diminished when compared with the wild-type animals (FIG. 1e). The lipid profiles of male mice were in line with those observed in females (FIG. 5).

As such, the lipid profile of the Usf1−/− mice appears to be the opposite of that observed in human metabolic syndrome. Accordingly, Usf-1 is a promising target for treating human metabolic syndrome indicated by elevated cholesterol and triglyceride levels. Therefore, a method to treat human metabolic syndrome is suggested by inhibiting Usf-1 in human cells.

Figure 10:
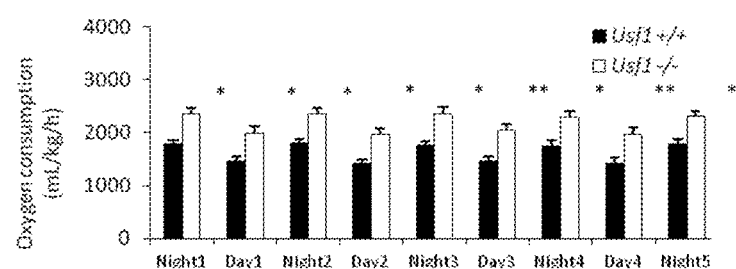
FIG. 10. Increased metabolic rate in Usf1 −/− mice in thermoneutral (+30° C.) conditions. Measurement of (A) oxygen consumption, (B) carbon dioxide production and (C) respiratory exchange ratio in chow-fed male mice, twelve months of age. N=4/4. * P<0.001,  P<0.01, * P<0.05. All values are mean±s.e.m.
Figure 10:
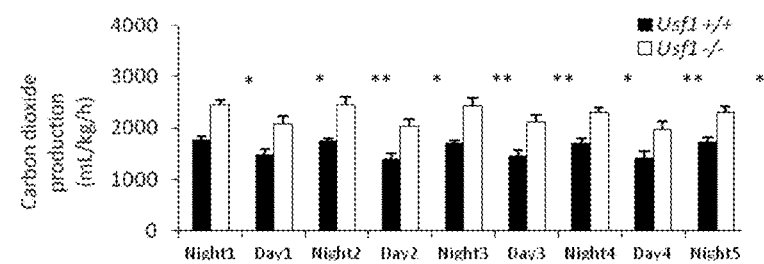
Figure 10:
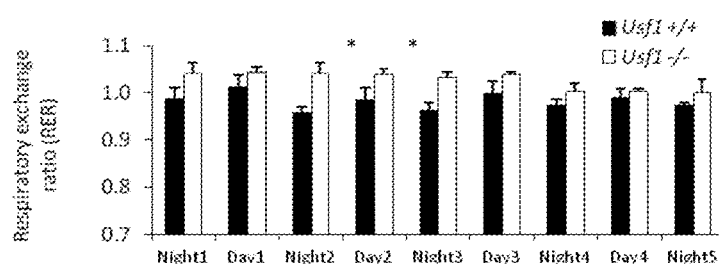

We next studied whether the reduced triglyceride levels in Usf1−/− mice could be due to decreased very low density lipoprotein (VLDL) production by the liver or elevated clearance of triglyceride-rich lipoproteins (TRLs) from the circulation. The activity of post-heparin plasma lipoprotein lipase in the Usf1−/− mice was increased by 30% indicating that TRLs are cleared from the serum of Usf1−/− mice in a more efficient manner (FIG. 10. Moreover, the hepatic VLDL production rate was decreased in Usf1−/− mice (FIG. 1g-h). These findings thus demonstrate that both improved TRL clearance and reduced VLDL secretion from the liver contribute to the reduced serum triglyceride levels in Usf1−/− mice.

Example 2. USF-1 Deficiency or Inhibition of Usf-1 Activity Improves the Efficacy of High Density Lipoprotein (HDL) Particles as Cholesterol Acceptors We then studied whether the elevated HDL levels in the Usf1−/− mice are associated with enhanced macrophage cholesterol efflux. We silenced Usf1 in human THP-1 macrophages by lentiviral RNA (shUSF1) and used serum collected from both Usf1+/+ and Usf1−/− mice as cholesterol acceptor. The knockdown of Usf1 in THP-1 macrophages improved the cholesterol efflux capacity of THP-1 cells to mouse serum, derived from both Usf1−/− and Usf1+/+ mice (FIG. 1i). Moreover, the serum from Usf1−/− mice proved to be a better cholesterol acceptor than serum obtained from Usf1 +/+ mice in both USF1 silenced and non-targeted cells (FIG. 1i). We next isolated HDL particles from the sera of both Usf1+/+ and −/− mice. The use of Usf1−/− derived HDL particles as acceptors in cells treated with either non-targeting or Usf1 silencing shRNAs resulted in enhanced cholesterol efflux indicating that the HDL particles of the Usf1−/− mice are functionally more efficient (FIG. 1j). Improved HDL composition is associated with favorable cardiovascular outcomes in humans[10]. We subsequently studied whether differential composition of the Usf1−/− mice derived HDL particles could explain their enhanced cholesterol efflux capacity. The compositional analysis of the HDL particles of Usf1−/− mice provided two major insights. First, the HDL particles from Usf1−/− mice were more enriched with phospholipids, and second, the proportional amount of apolipoprotein A1 was decreased indicating a high PL/Apo-AI ratio (FIG. 1k). Fournier has previously reported that the phospholipid content of HDL particles is the major component modulating cholesterol efflux potential[11]. Thus, our findings signal that the efficiency of HDL particles derived from Usf1−/− mice as cholesterol acceptors is ascribed to their elevated phospholipid content. Accordingly it is suggested that Usf-1 inhibition has a high potential as a method to modify cholesterol efflux and treat patients with high cholesterol levels.

Figure 2:
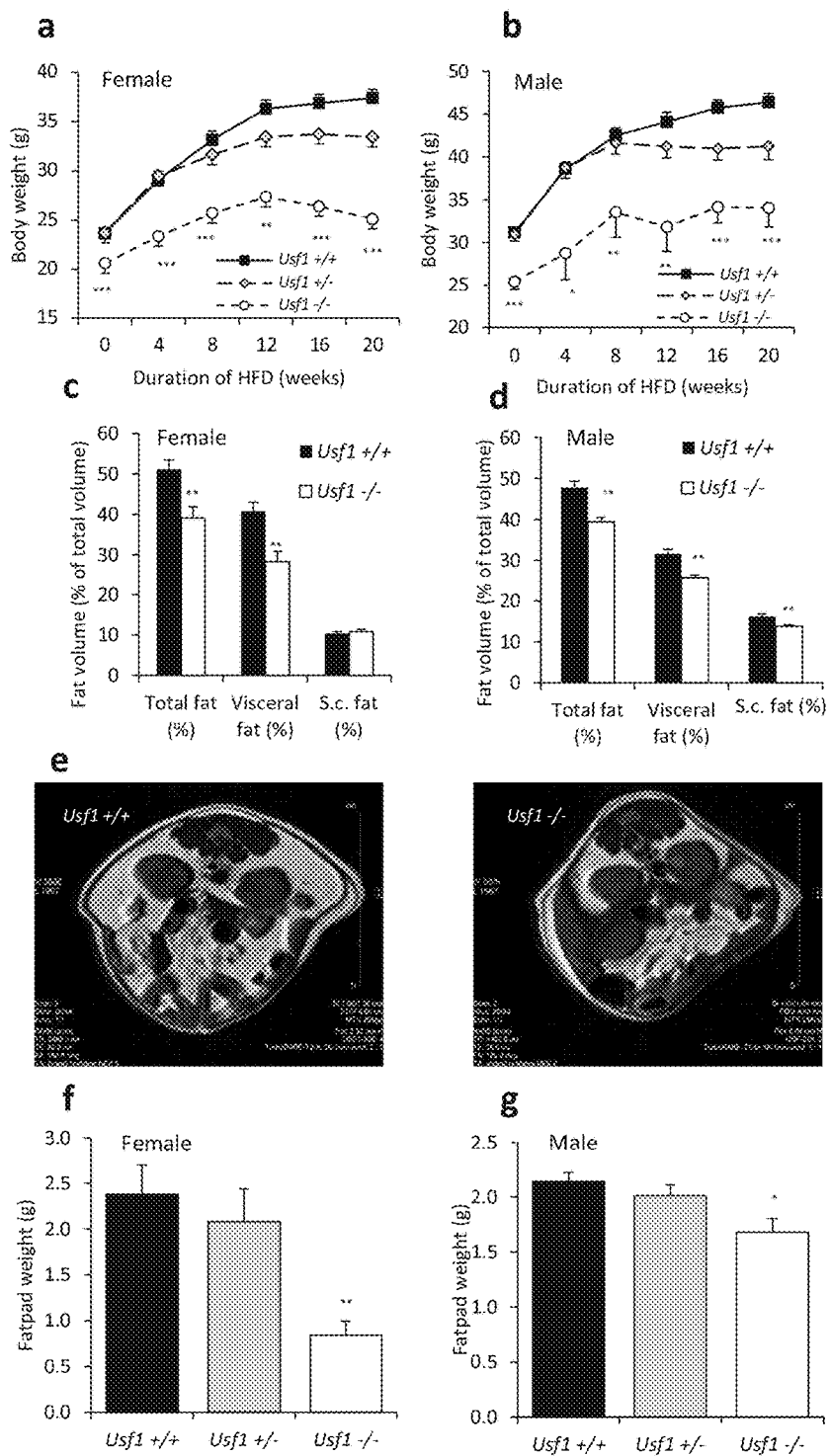
FIG. 2. Deficiency of Usf1 protects against high-fat diet induced obesity. (a) Weights of female mice during HFD. N=23/22. (b) Weights of male mice during HFD. N=1817. (c) Fat volume (%) of female mice at 20 weeks after HFD. N=6/6. (d) Fat volume (%) of male mice at 20 weeks after HFD. N=6/3. (e) A representative MRI image from each genotype group is shown in female mice. The fat pad weights are also reduced in both female (f) (N=14/9), and male (g) (N=1815) Usf1 −/− mice after 20 weeks of HFD. In H&E stained specimens obtained from epididymal adipose tissue (h), the adipocyte size in Usf1 −/− mice is smaller after 20 weeks of HFD (i), featuring a higher frequency of small adipocytes (j). Female mice, N=17/12. * P<0.001,  P<0.01, * P<0.05. All values are mean±s.e.m.
Figure 2:
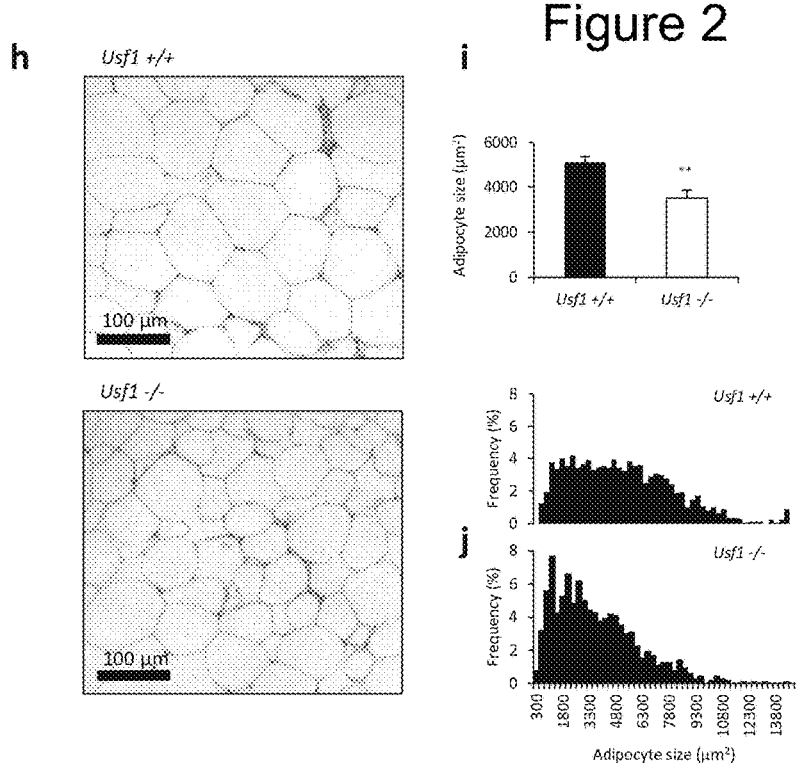

Example 3. USF-1 Deficiency or Inhibition of Usf-1 Activity Protects Against Obesity We then analyzed whether the Usf1−/− mice differ by weight from their Usf1+/+ littermates. Before the start of the 20-week HFD, the Usf1−/− mice were 12% (males 19%) leaner than Usf1+/+ controls (FIG. 2a-b). Strikingly, the Usf1−/− mice were protected against obesity during the HFD, as evidenced by the 32% (males 27%) difference in body weight at the end of the diet. In order to verify that this dramatic effect of Usf1 on body weight was due to reduced body fat content of the mice, we measured the adipose depots of the mice by magnetic resonance imaging (MRI). Quantification of mouse MRI images after 20 week of feeding with HFD demonstrated that the body fat percentage in Usf1−/− mice was reduced by 24% (males 17%) when comparing with the Usf1+/+ mice (FIG. 2c-e). Importantly, the reduced volume of the metabolically more deleterious visceral fat content is likely to be the predominant factor contributing to the reduced adiposity in these animals rather than subcutaneous adipose tissue, which showed no genotype dependency probably owing to the generally reduced adiposity of the knockouts (FIG. 2c-e). We further validated these results by the weighing of epididymal fat pads in dissected tissues from euthanized animals and observed a striking 65% decrease (males 22%) in the fat pad weights in the Usf1−/− mice (FIG. 2f-g). Quantification of adipocyte cross-sectional areas from epididymal adipose tissue depots displayed a reduction in adipocyte size and a higher proportion of small adipocytes in Usf1−/− mice (FIG. 2h-j). Thus, the Usf1−/− mice appear to be resistant against HFD induced adipocyte hypertrophy.

As a conclusion Usf-1 is a highly preferred target for treating and preventing obesity. A method to prevent and treat obesity by inhibiting Usf-1 in humans is suggested. Usf-1 inhibitors are suggested for preparation of medication for treating and/or preventing obesity.

Figure 3:
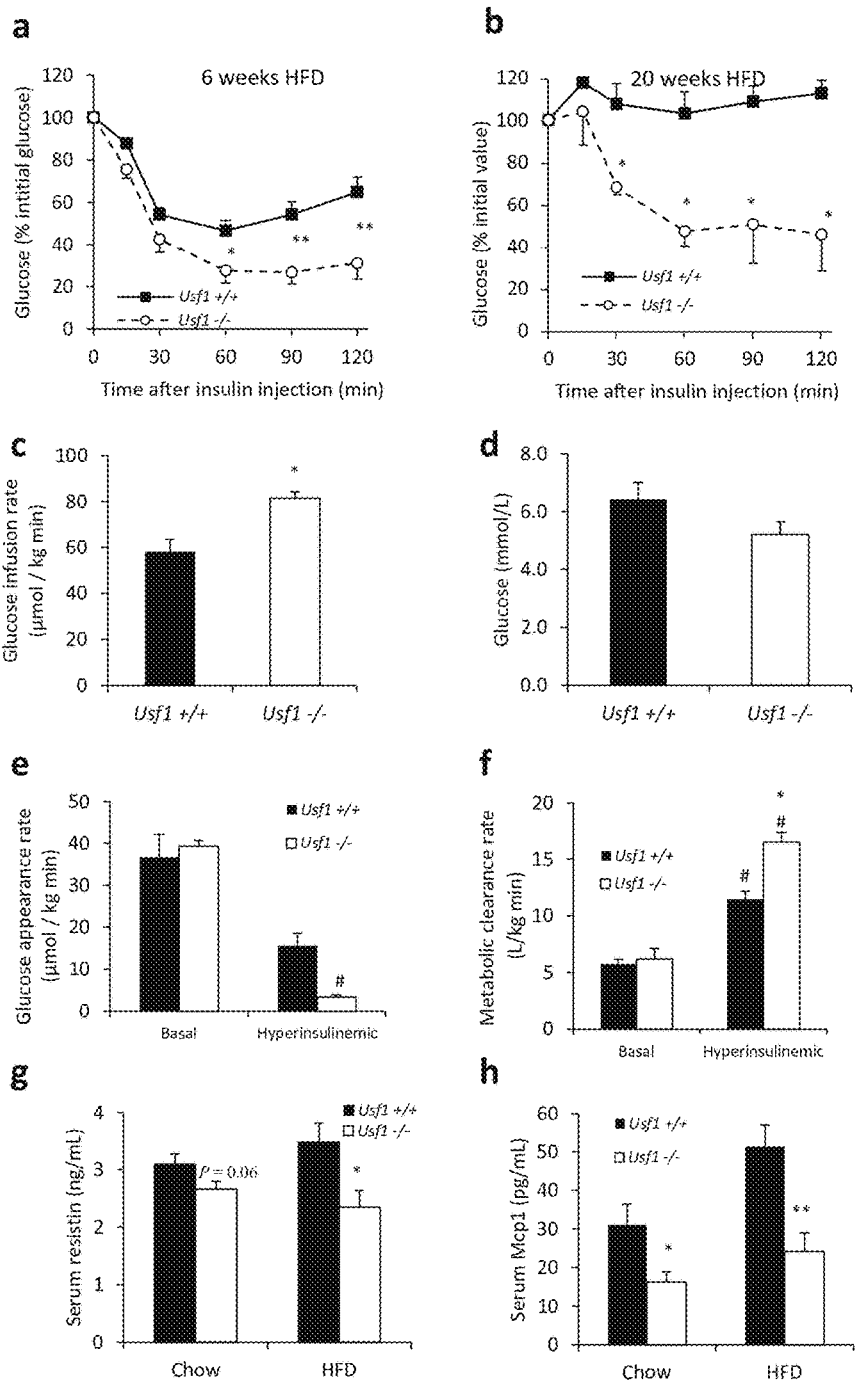
FIG. 3. The absence of Usf1 alleviates metabolic complications associated with obesity. (a) Insulin tolerance test after 6 weeks of HFD. Male mice, N=6/5. (b) Insulin tolerance test performed after 20 weeks of HFD. Male mice, N=8/2. (c-f) Glucose infusion rate (GIR) and circulating glucose levels during the last 20 min of the hyperinsulinemic euglycemic clamp, and glucose appearance rate and metabolic clearance rate during the basal and hyperinsulinemic period of the clamp. Symbol * represents comparison between Usf1+/+ and Usf1−/− mice, and symbol # represents comparison between basal and hyperinsulinemic conditions within a genotype group. N=4/2. (g-j) Serum resistin, Mcp1, TNF-α, and adiponectin in male mice on a chow diet and after 8 weeks on HFD. N=11/11 chow; N=14/7 HFD. (k) Representative images of liver histology using Oil Red O from Usf1 male mice after 6 weeks of HFD. (l) Liver triglyceride content in male mice after 6 weeks of HFD. N=17/10. (m) Aortic lesion area in Usf1+/+ Ldlr−/− and Usf −/− Ldlr−/− mice as indicated by Sudan IV staining. The light micrograph shows en face views of 2 aortas, each derived from a representative mouse of each group. The dashed line indicates the assumed boundary between aortic arch and descending thoracoabdominal aorta. Male mice 20 weeks after HFD. (n) Quantification of the lesion area in the descending aorta. En face images, male mice 20 weeks after HFD. N=8/8. (o) Quantification of the lesion area in the aortic arch. En face images, male mice 20 weeks after HFD. N=8/8. (p) Oil Red O stained sections from the aortic root. Representative images are shown from both Usf1 +/+ Ldlr −/− and Usf1 −/− Ldlr −/− genotype groups. Male mice 20 weeks after HFD. (q) Quantification of the lesion area in the aortic root. Cross-sectional images, male mice 20 weeks after HFD. N=8/8. * P<0.001,  P<0.01, * P<0.05. All values are mean±s.e.m.
Figure 3:
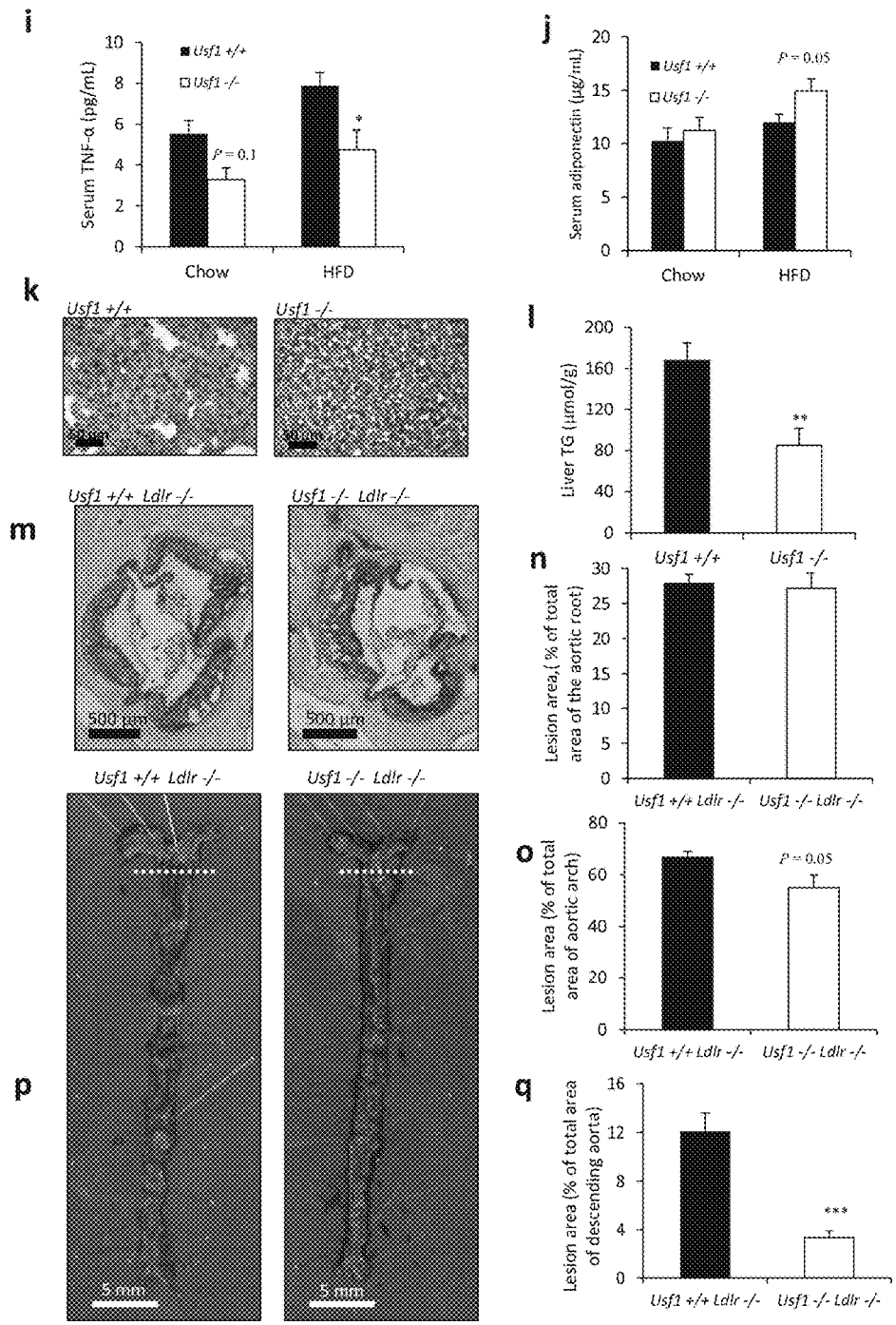

Example 4. USF-1 Deficiency or Inhibition of Usf-1 Activity Protects Against Insulin Resistance We next investigated whether the lean phenotype of Usf1−/− mice protects them from the metabolic complications associated with increased adiposity. Insulin resistance frequently coexists with obesity, and during insulin tolerance test, the Usf1−/− mice were more responsive to insulin treatment than control mice after 6 weeks of feeding with HFD (FIG. 3a). After 20 weeks of HFD, the Usf1−/− mice were still insulin sensitive while the Usf1+/+ males had completely lost their responsiveness to insulin administration, indicating that the Usf1−/− mice were protected against the severe HFD induced insulin resistance (FIG. 3b). Furthermore, we performed the gold-standard method for assessing insulin sensitivity, the hyperinsulinemic euglycemic clamp study, on both Usf1+/+ and Usf1−/− mice after feeding 6 weeks of HFD. Glucose infusion rate necessary to maintain euglycemia was 29% higher in Usf1−/− mice in the presence of similar glucose levels, indicating improved insulin sensitivity (FIG. 3c). There was no significant difference in basal glucose appearance rate (GAR) and metabolic clearance rate (MCR) between Usf1+/+ and Usf1−/− mice (FIG. 3e-f), but during hyperinsulinemic period, GAR was decreased by 91% in Usf1−/− mice and 61% in Usf1+/+ mice, and MCR was increased by 166% in Usf1−/− mice and 98% in Usf1+/+ mice, confirming the protective effect of Usf1 deficiency against HFD induced insulin resistance (FIG. 3e-f).

As a conclusion Usf-1 is a highly preferred target for treating and preventing insulin resistance which often coexists with or results from obesity. A method to prevent and treat insulin resistance by inhibiting Usf-1 in humans is suggested. Usf-1 inhibitors are suggested for preparation of medication for treating and/or preventing insulin resistance.

Figure 6:
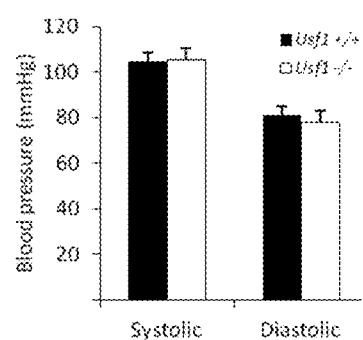
FIG. 6. Blood pressure levels are similar between Usf1 +/+ and Usf1 −/− mice. Females, HFD after 20 weeks N=8/8 * P<0.001,  P<0.01, * P<0.05. All values are mean±s.e.m.

Example 5. USF-1 Deficiency or Inhibition of Usf-1 Activity Protects Against Chronic Metabolic and Vascular Inflammation Obesity results in a chronic inflammatory state in metabolically active tissues, and leads to increased production of myriad chemoattractant and inflammatory mediators. Plasma protein levels of resistin, Ccl2 (MCP-1), and TNF-α were significantly reduced (FIG. 3g-i) and adiponectin levels modestly elevated (FIG. 3j) in Usf1−/− mice signifying that they were protected against chronic metabolic and vascular inflammation. This protection was also mirrored by the reduction in fatty infiltration of the liver in Usf1−/− mice (FIG. 3k), which displayed a 49% reduction in their hepatic triglyceride contents after feeding HFD for 6 weeks (FIG. 3l). Elevated blood pressure is also a component of the metabolic syndrome. The absence of Usf1 did not affect blood pressure levels in the mice (FIG. 6).

As a conclusion Usf-1 is a potential target for treating and preventing metabolic and vascular inflammation caused by obesity. A method to prevent and treat chronic metabolic and vascular inflammation by inhibiting Usf-1 in humans is suggested. Usf-1 inhibitors are suggested for preparation of medication for treating and/or preventing metabolic and vascular inflammation.

Figure 7:
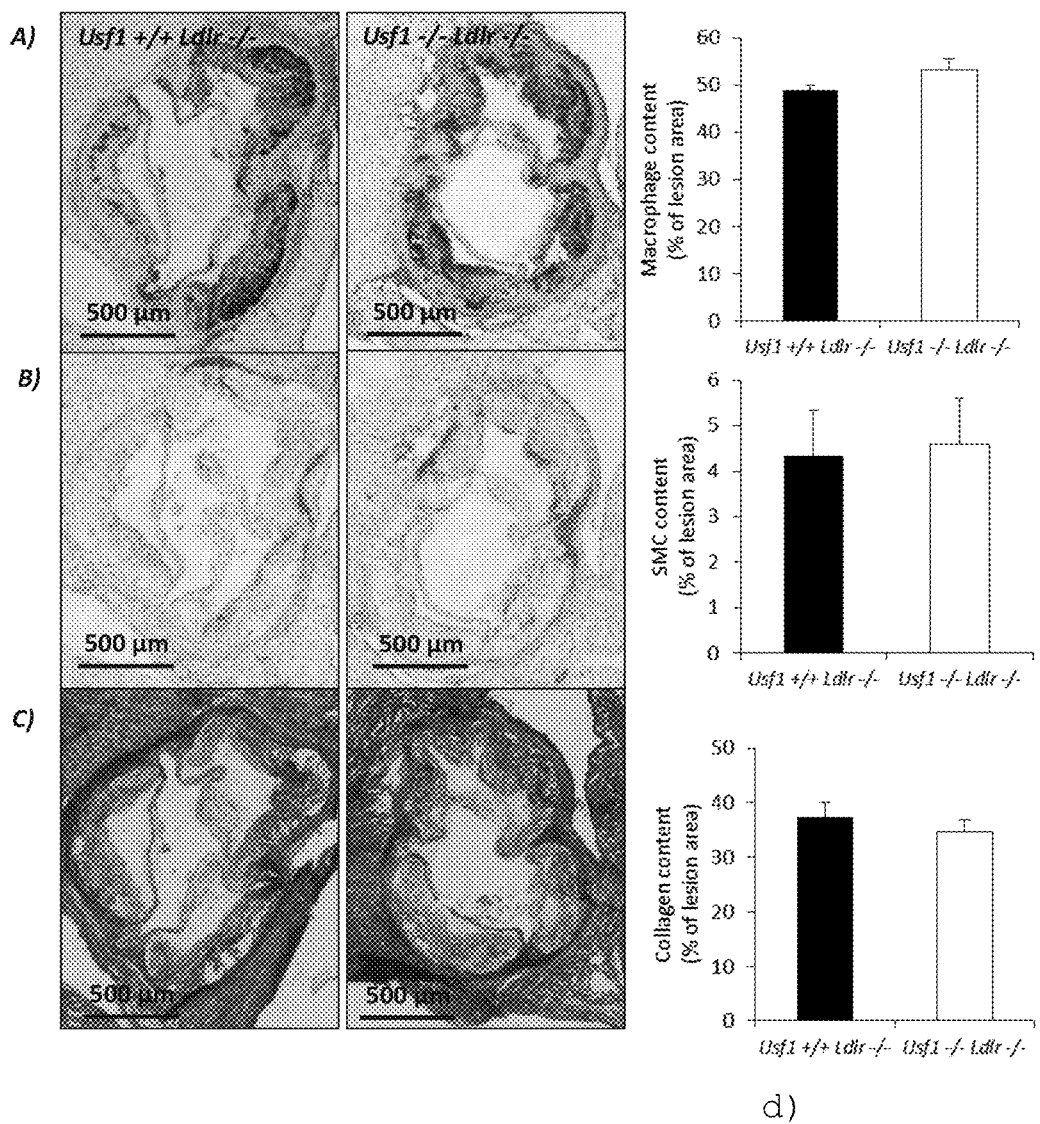
FIG. 7. Lesion area in the aortic root (A), and macrophage (B), smooth muscle cell (SMC) (C), and collagen (D) content in the aortic root lesions of Usf1 +/+ Ldlr −/− and Usf1 Ldlr −/− mice after 20 weeks of HFD feeding.

Example 6. USF-1 Deficiency or Inhibition of Usf-1 Activity Reduces Atherosclerosis Atherosclerosis is one of the most important comorbidities associated with type 2 diabetes mellitus, and the process is accelerated by metabolic disturbances and chronic low-grade vascular inflammation. We next studied whether the lower burden of metabolic derangements in Usf1−/− mice protects them against atherosclerosis. To induce atherosclerosis, we crossed Usf1−/− mice into atherosclerosis prone Ldlr −/− strain rather than Apoe −/− strain due to an earlier report identifying human APOE a downstream target of USF1[12]. After feeding the mice HFD for 20 weeks, we quantified atherosclerotic lesion areas in both Usf1+/+ Ldlr−/− and Usf1−/−Ldlr−/− double knockouts (FIG. 3m-q). The deficiency of Usf1 dramatically reduced atherosclerosis in the thoracoabdominal aorta as demonstrated by a 72% decrease in the lesion area in the longitudinal en face preparations of Usf1−/−Ldlr−/− mice as compared to Usf1+/+Ldlr−/− mice (FIG. 3*m-o*). The lesion area in the aortic root and plaque composition, marked by the quantification of macrophages, smooth muscle cells and collagen, were similar across the genotypes (FIG. 3*p-q*, FIG. 7).

As a conclusion Usf-1 is a potential target for treating and preventing atherosclerosis. A method to prevent and treat atherosclerosis by inhibiting Usf-1 in humans is suggested. Usf-1 inhibitors are suggested for preparation of medication for treating and/or preventing atherosclerosis.

Figure 4:
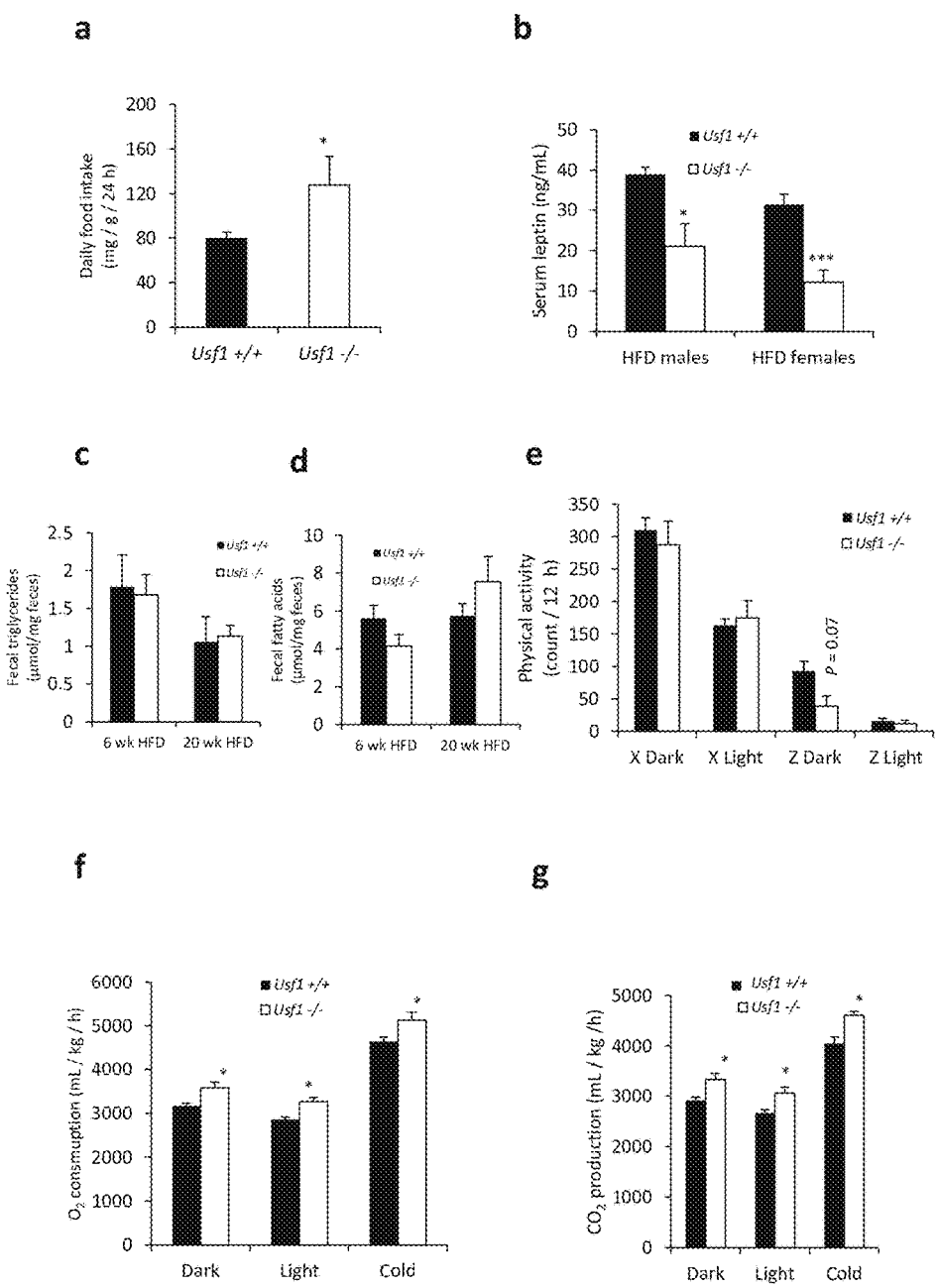
FIG. 4. Increased metabolic rate in Usf1−/− mice. (a) Daily food intake in male mice, 20 weeks after HFD at +20° C. N=9/4. (b) Leptin levels in male and female mice after 8 weeks of HFD. N=14/7/14/11. (c) Fecal triglyceride content of male mice after 6 weeks and 20 weeks of HFD. N=5/4/7/3. (d) Fecal fatty acid content of male mice after 6 weeks and 20 weeks of HFD. N=5/4/7/3. (e) Physical activity of the mice in horizontal (X) and vertical (Z) dimensions in male mice, 20 weeks after HFD at +20° C. N=9/4. (f) Oxygen consumption and (g) carbon dioxide production in male mice, 20 weeks after HFD at +20° C. N=9/4. (h) Organ distribution of [$^3$H] oleate (free fatty acid) 15 min after tail-vein injection. Female mice, chow diet, N=4/6. (i) Organ distribution of [$^3$H] triolein (triglyceride) 15 min after tail-vein injection. Male mice, 6 weeks after HFD, N=9/6. (j) Organ distribution of [$^{14}$C] cholesterol oleate (representing TRL holoparticle) 15 min after tail-vein injection. Male mice, 6 weeks after HFD, N=9/6. (k) Organ distribution of [$^3$H] triolein (triglyceride) 15 min after tail-vein injection in the absence and presence of tetrahydrolipstatin (THL). Male mice, 6 weeks after HFD, N=6/5. (l) H&E staining of brown adipose tissue. Representative images of chow-fed male mice are shown. (m) Lipid content of brown adipose tissue as quantified from electron micrographs. Male mice, chow diet. N=4/4. (n) Lipid droplet size in brown adipose tissue as quantified from electron micrographs. Male mice, chow diet. N=4/4. (o)-(p) Size distribution of lipid droplets between Usf1+/+ and Usf1−/− mice. Male mice, chow diet. * P<0.001,  P<0.01, * P<0.05. All values are mean±s.e.m.
Figure 4:
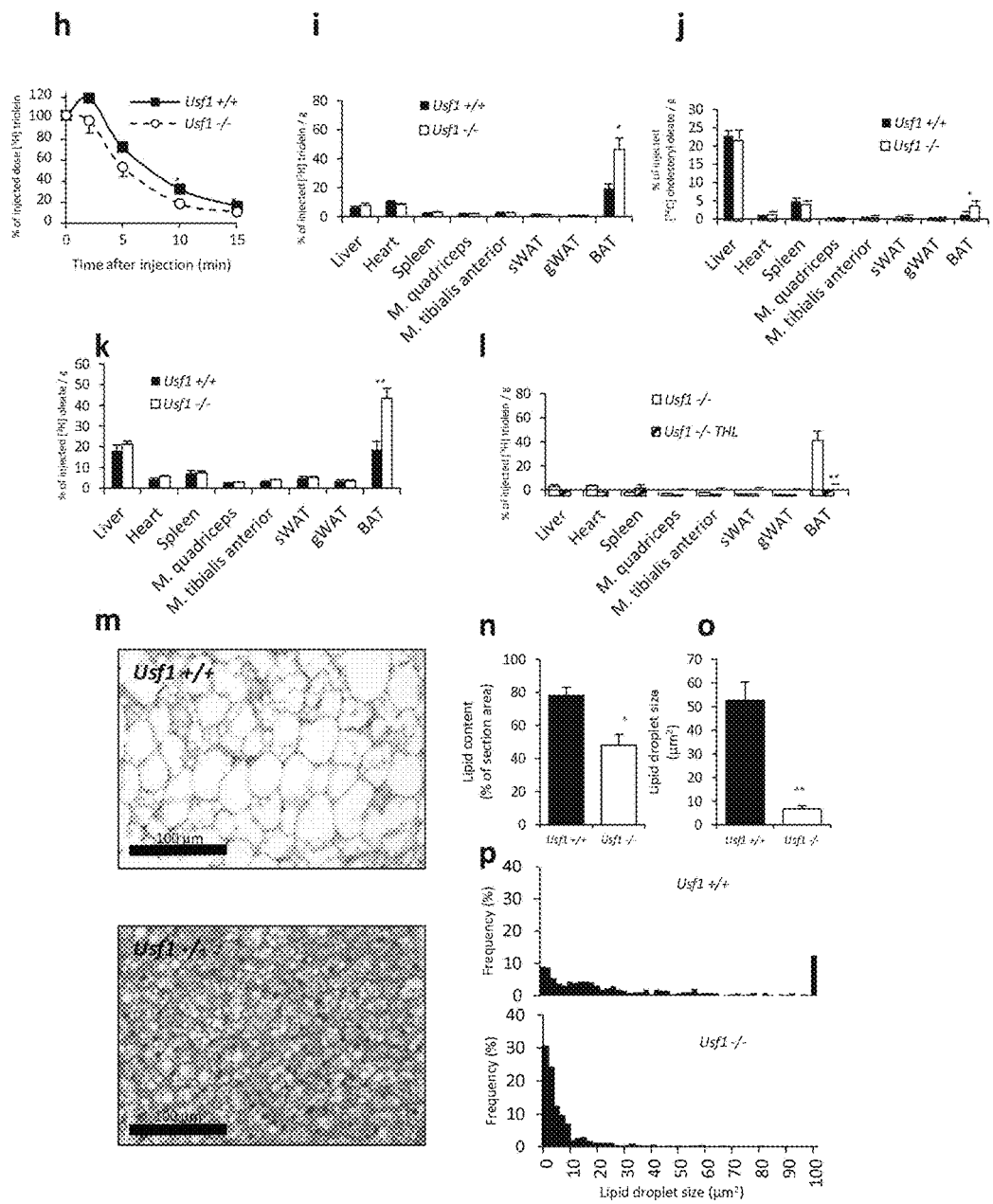
Figure 8:
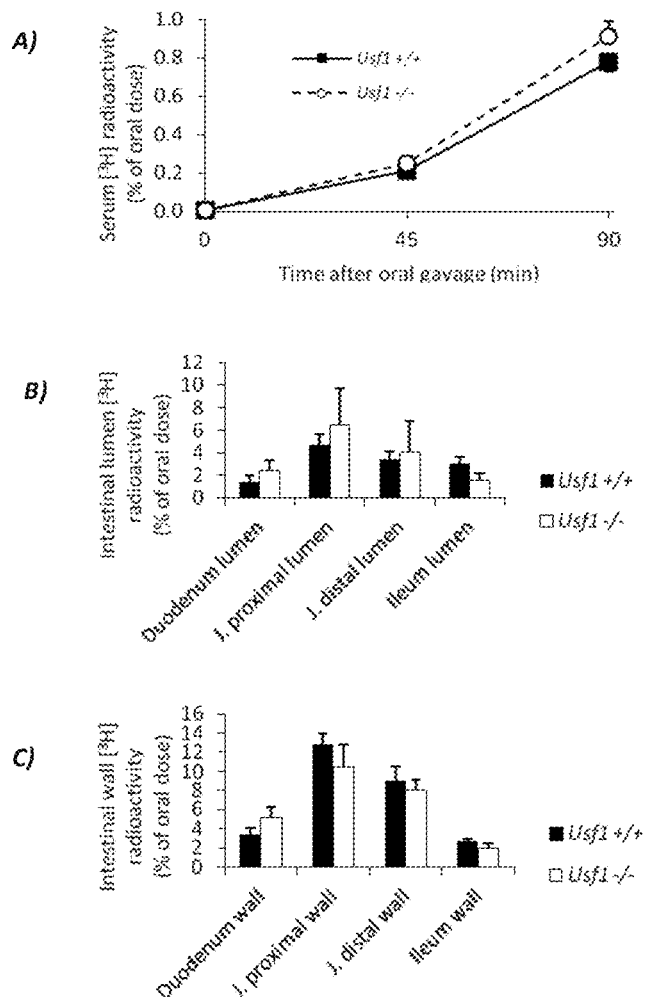
FIG. 8. Intestinal absorption of [$^3$H] triolein 90 minutes after oral gavage. [$^3$H] derived radioactivity in (A) serum, (B) lumen, and (C) tissue of small intestine. Animals are female mice on a chow diet. N=9/4. * P<0.001,  P<0.01, * P<0.05. All values are mean±s.e.m.
Figure 9:
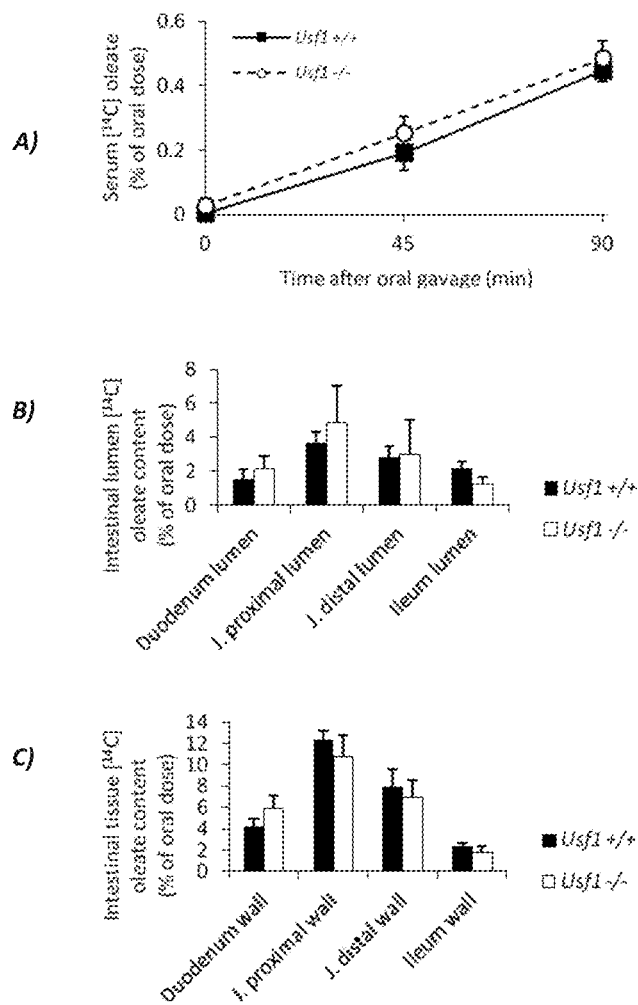
FIG. 9. Intestinal absorption of [$_{14}$C] oleate 90 minutes after oral gavage. [$^{14}$C] derived radioactivity in (A) serum, (B) lumen, and (C) tissue of small intestine. Animals are female mice on a chow diet. N=9/4. * P<0.001,  P<0.01, * P<0.05. All values are mean ±s.e.m."

Example 7. USF-1 Deficiency or Inhibition of Usf-1 Activity Increases Energy Expenditure We next went on to examine mechanisms that could prevent the excessive weight gain of Usf1−/− mice during HFD and related metabolic complications. Despite their markedly lower body weight and reduced adiposity, the Usf1−/− mice were hyperphagic consuming 60% more food energy than Usf1+/+ mice on a high-fat diet (FIG. 4*a*). While unexpected, this finding is consistent with Usf1−/− mice having reduced serum levels of leptin (FIG. 4*b*), an appetite suppressing hormone whose secretion from the adipose tissue is directly proportional to fat mass. We then investigated whether the reduced adiposity of Usf1−/− mice reflects their impaired intestinal lipid absorption as absorption is known to contribute to the supply of fat for the adipose tissue. In chow-fed animals, there was no difference in the transfer of lipids from small intestine to the circulation after an oral gavage (FIGS. 8-9). Moreover, the triglyceride and fatty acid concentrations of the feces were similar between Usf1+/+ and Usf1−/− mice after both 6 weeks and 20 weeks of HFD feeding (FIG. 4*c-d*) suggesting that biological processes outside the gastrointestinal tract are likely to explain the lean phenotype of the Usf1−/− mice.

Figure 11:
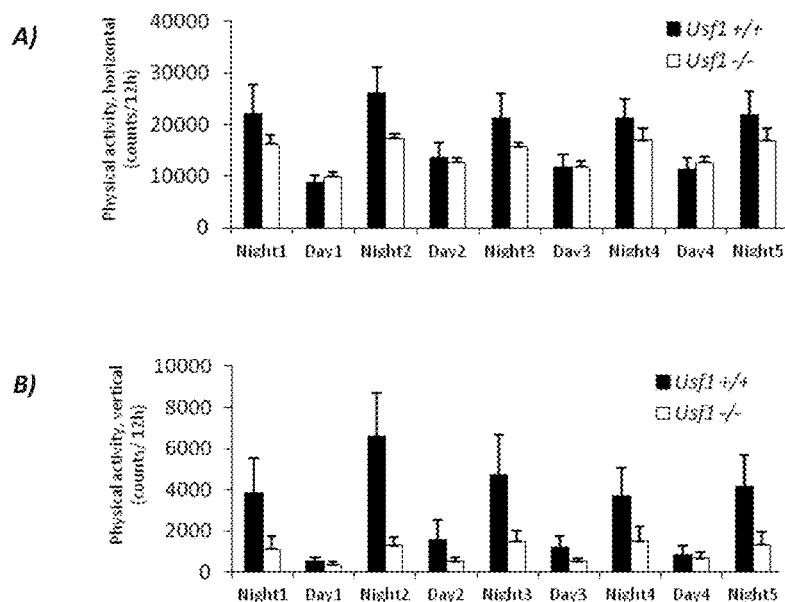
FIG. 11. Increased metabolic rate in Usf1 −/− mice in thermoneutral (+30° C.) conditions. Measurement of (A) horizontal physical activity and (B) vertical physical activity in chow fed male mice in thermoneutral conditions. N=4/4. * P<0.001,  P<0.01, * P<0.05. All values are mean±s.e.m.

Our subsequent measurements of physical activity indicated that the Usf1−/− mice were in fact less active than the control mice (FIG. 4*e*, FIG. 11). Despite this counterintuitive finding, measurements using CLAMS metabolic cages revealed that Usf1−/− mice have increased energy expenditure. In room temperature (+20° C.), the Usf1−/− mice had 13% higher oxygen consumption (FIG. 4*f*) and 14% higher carbon dioxide production (FIG. 4*g*) than the control mice. We further validated these findings in mice housed at +30° C. temperature (FIGS. 6-7), which is generally considered to be thermoneutral for mice. Reproducing our findings in thermoneutral conditions indicates that the higher $VO_2$ and $VCO_2$ are not due to altered insulation capacity, but truly reflect the increased metabolic rate in Usf1−/− mice.

As a conclusion Usf-1 is a potential target for weight loss via increasing metabolic rates and energy expenditure. A method to increase energy expenditure by inhibiting Usf-1 in humans is suggested. Usf-1 inhibitors are suggested for preparation of medication for weight loss.

Example 8. USF-1 Deficiency or Inhibition of Usf-1 Activity Activates the Brown Adipose Tissue Brown adipose tissue (BAT) is a key organ regulating whole-body energy expenditure, and its pathophysiological relevance in humans is established. The activity of BAT is inversely proportional to body fat content and it has also been shown to control plasma lipids[13]. To assess whether BAT contributes to lipid uptake in Usf1−/− mice, we injected [$^3$H]-oleate into the tail vein of the mice which we sacrificed after 15 minutes. The organ distribution to BAT of [$^3$H]-derived radioactivity was markedly increased in Usf1−/− mice, indicating a preferential BAT mediated uptake of circulating fatty acids (FIG. 4*h*). To study whether triglyceride rich lipoproteins (TRL) are more avidly processed by BAT in Usf1−/− mice, the mice were additionally injected with [$^3$H]-triolein and [$^{14}$C]-cholesteryl oleate double-labeled TG-rich VLDL-like emulsion particles. Again, we observed a significant rise in [$^3$H]-triolein uptake into BAT of Usf1−/− mice as compared to Usf1+/+ controls (FIG. 4*i*), indicating that Usf1 deficiency is associated with enhanced VLDL-TG uptake into BAT. Similarly, the [$^{14}$C]-cholesteryl oleate derived radioactivity originating from the TRL particle core was 2-fold higher in the BAT of Usf1−/− mice (FIG. 4*j*). Our data thus demonstrate that in addition to taking up free fatty acids and triglycerides in a more efficient manner, the BAT of Usf1−/− mice also more avidly endocytoses TRLs as holoparticles. As such, the deficiency of Usf1 mimics the acute effects of cold exposure on lipoprotein turnover.

Figure 12:
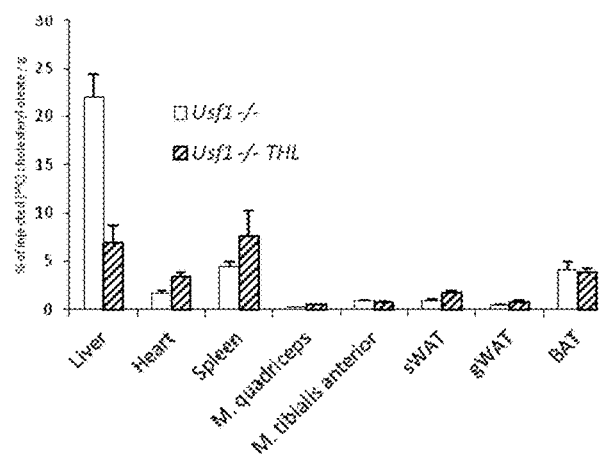
FIG. 12. Uptake of [$^{14}$C] cholesterol oleate to BAT is not influenced by tetrahydrolipstatin treatment. N=4/5 * P<0.001,  P<0.01, * P<0.05. All values are mean±s.e.m.

We then examined whether lipoprotein lipase, the key enzyme involved in the organ uptake of triglyceride rich lipoproteins, is mediating the increased uptake of TRLs into BAT of Usf1−/− mice. Injection of tetrahydrolipstatin (THL), a selective inhibitor of LPL before the administration of TRLs, completely eliminated the uptake of TRLs into BAT (FIG. 4*k*), demonstrating that the elevated TRL uptake to BAT in Usf1−/− mice is facilitated by LPL function. The uptake of [$^{14}$C]-cholesteryl oleate into the BAT was unaffected in Usf1−/− mice in the presence of THL, demonstrating that LPL-independent pathways are required for TRL holoparticle uptake to BAT (FIG. 12). These findings strongly link the BAT activation of Usf1−/− mice to their beneficial serum lipid profile with decreased triglycerides and elevated LPL activity (FIG. 1*e-f*).

Figure 13:
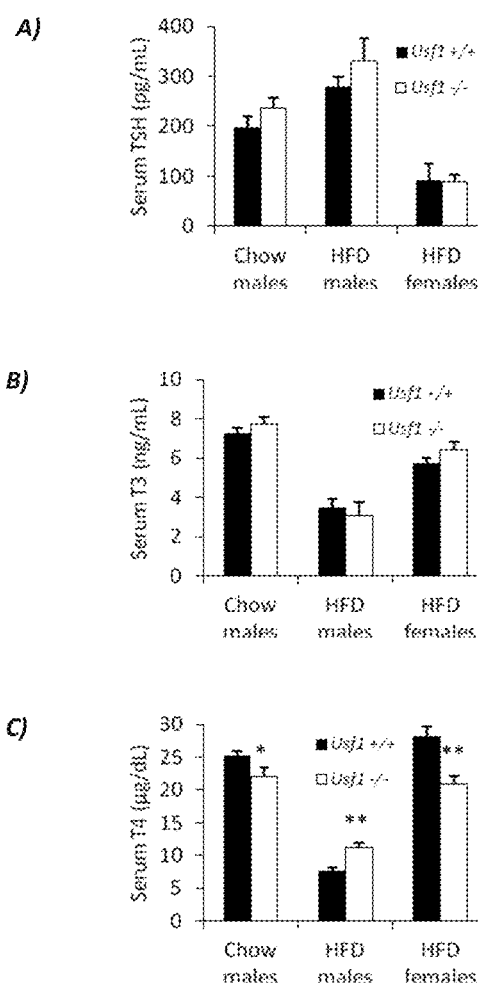
FIG. 13. (a)-(c) Thyroid hormone measurements of Usf1 −/− mice. For chow males, N=11/11; for 8-week HFD males, N=14/7; for 8-week HFD females, N=14/11. * P<0.001,  P<0.01, *P<0.05. All values are mean±s.e.m.

Excessive production of thyroid hormones is known to cause a hypermetabolic state with increased energy expenditure, and weight loss, and thyroid activity is reported to influence BAT activity. In Usf1−/− mice, the levels of TSH and T3 were unaltered (FIG. 13). While Usf1−/− males had elevated serum levels of T4 on a HFD, the Usf1−/− females displayed reduced levels of T4 (FIG. 13), while still taking up more fatty acids into BAT (FIG. 4*h*). These results make the elevated thyroid function unlikely to account for the BAT activation in Usf1−/− mice.

As conclusion inhibition of Usf-1 is proposed as a target for activating the brown adipose tissue and positively affects the lipid metabolism of humans. Accordingly activation of BAT through Usf-1 inhibition is suggested to treat human metabolic syndrome.

Figure 14:
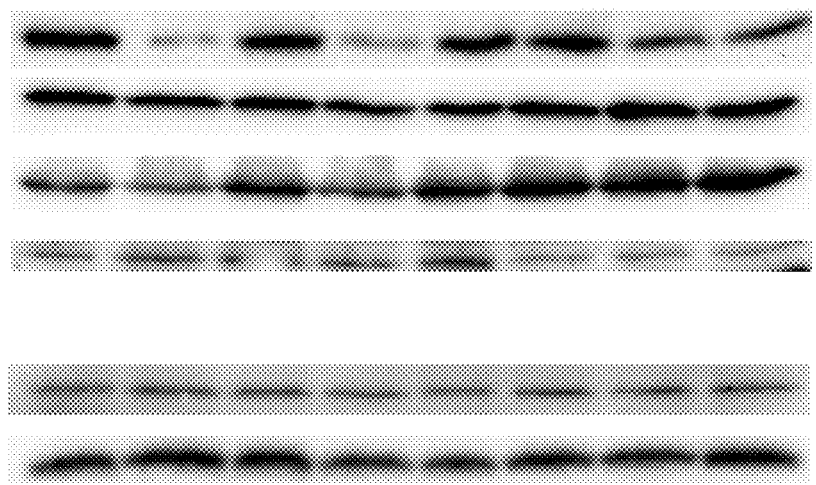
FIG. 14. (a)-(c) Western blot images and quantification of mitochondrial respiratory chain complexes and Ucp1. AU represents arbitrary unit. Animals are male mice on a chow diet for twelve months. N=4/4. * P<0.001,  P<0.01, * P<0.05. All values are mean±s.e.m FIG. 15. Transmission electron micrographs of BAT from male mice demonstrating the differing sizes of lipid droplets between Usf1 +/+ and Usf1 −/− mice. The 120× magnification applies to every panel.
Figure 14:
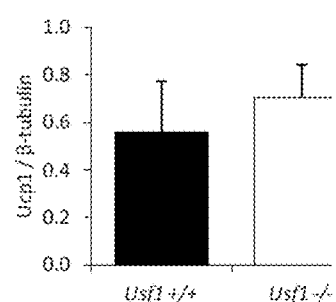
Figure 14:
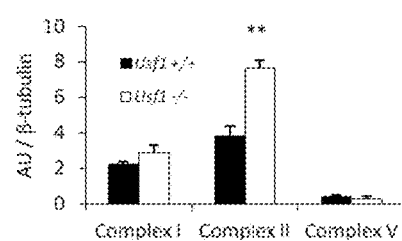
Figure 15:
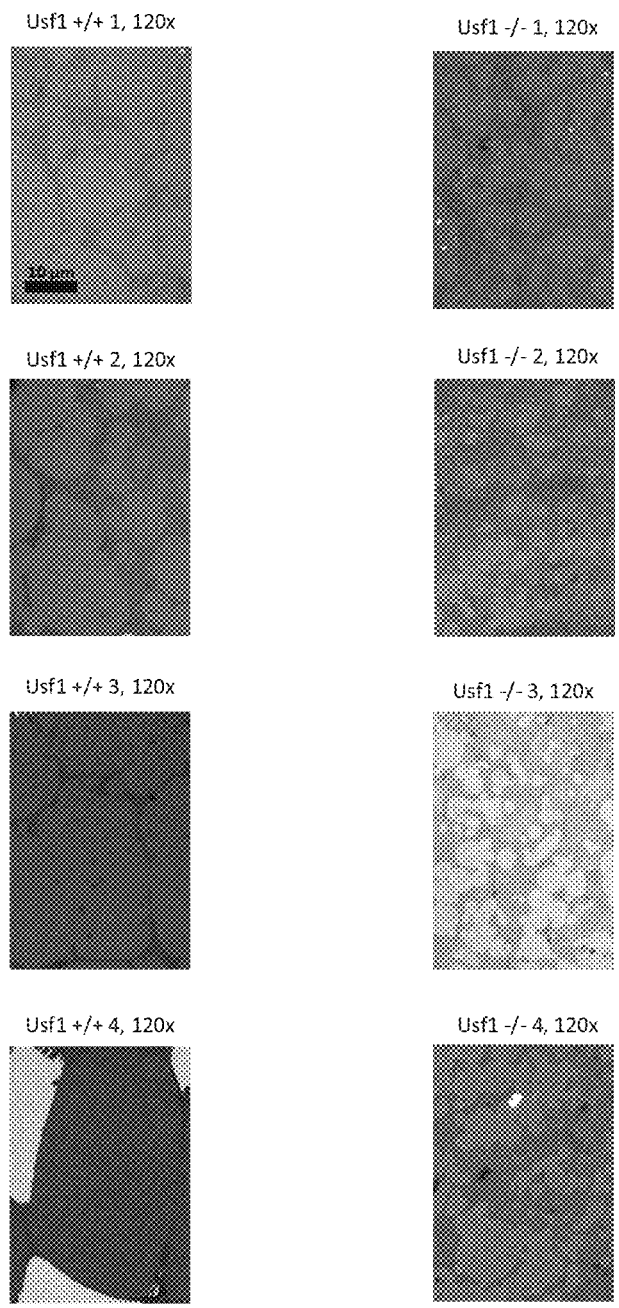

Example 9. USF-1 Deficiency or Inhibition of Usf-1 Activity Decreases the Average Size of Lipid Droplets in BAT The levels of Ucp1 protein were unchanged in BAT (FIG. 14*a-b*). We measured the levels of mitochondrial complexes from BAT, and observed that complex II protein was more abundant in the BAT Usf1−/− mice, in line with elevated $VO_2$ (FIG. 14*a,c*). Importantly, the lipid content of BAT was decreased by 37% in Usf1−/− mice as determined from transmission electron micrographs (FIG. 4*l-m*, FIG. 15). Furthermore, the average size of lipid droplets in BAT was decreased by a striking 87% (FIG. 4*n*, FIG. 15) with very small lipid droplets observed more frequently in Usf1−/− mice (FIG. 4*o*). Our findings thus demonstrate that the more efficient transfer of TRLs from blood to BAT in Usf1−/− mice does not result in excessive lipid accumulation in the BAT. Rather, they are more likely further metabolized by BAT in agreement with elevated $VO_2$ and $VCO_2$ observed in Usf1−/− mice. Based on the hallmarks of BAT activation observed in Usf1 deficient mice, it is plausible to draw parallel between Usf1 linked BAT directed lipoprotein clearance in mice and USF1 associations with plasma lipid levels in humans. Hence, it is suggested that disturbances in BAT activity could also underlie FCHL and other common human dyslipidemias.

As conclusion inhibition of Usf-1 is proposed as a target for activating the brown adipose tissue and positively affect the lipid metabolism of humans.

Example 10. Usf-1 Inhibition has a Key Role in Brown Adipose Tissue Metabolism

Here, we have further examined the role of USF1 inhibition in metabolism, and in particular, the role of brown adipose tissue. As previously stated, we have shown that the BAT of USF1 knockout mice takes up more lipids. Furthermore, the BAT is more active with larger lipid droplets in BAT.

Figure 16:
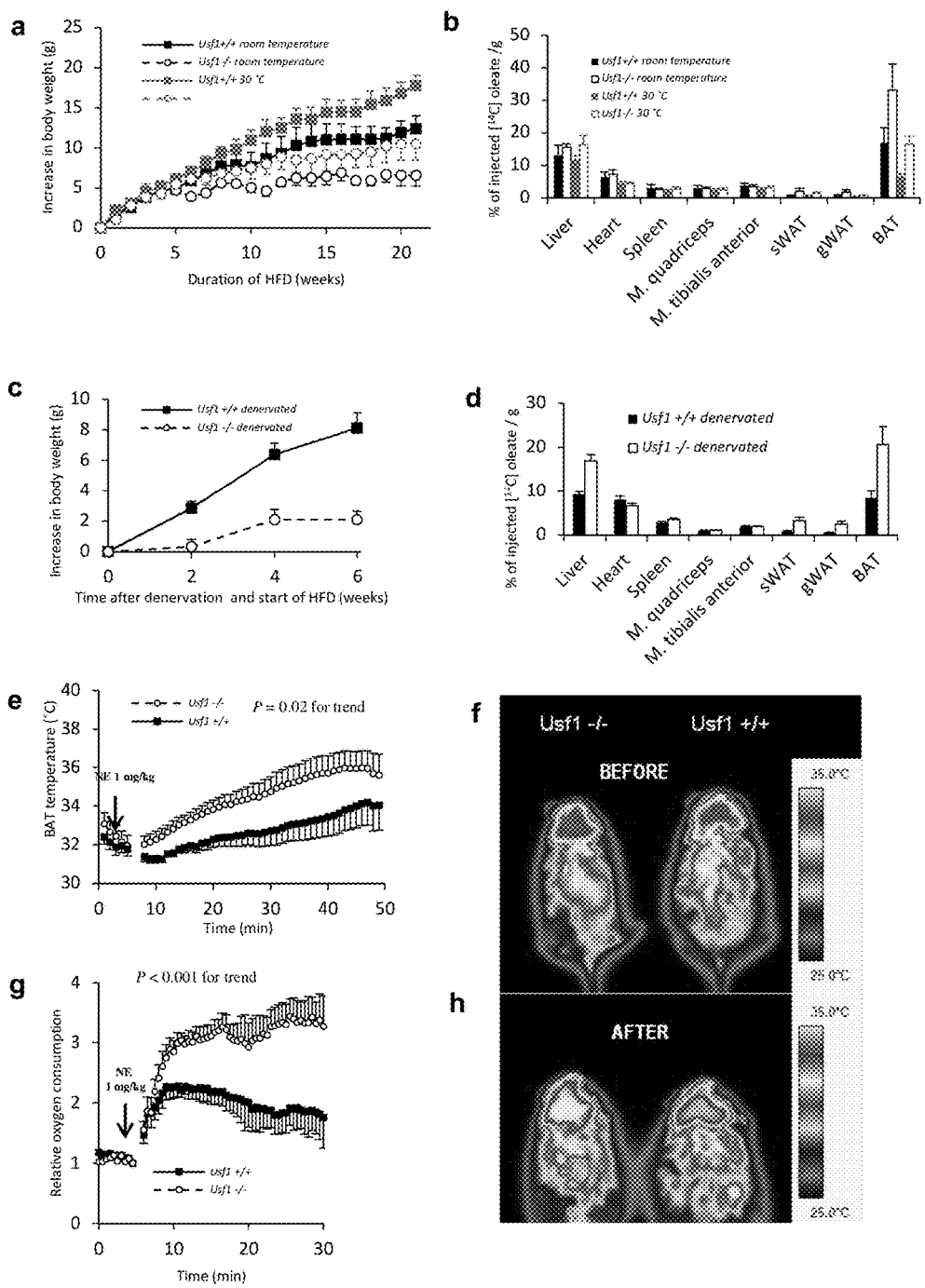
FIG. 16. The absence of Usf1 alleviates metabolic complications associated with obesity also in thermoneutral environment. a) Shows lower body weight increase in usf1−/1 mice also in thermoneutral environment. b) shows the BAT lipid uptake to be higher in usf1−/− mice also in thermoneutral temperature. c)-d) correspond to figures a) and b) in experiment where the mice were denervated. e-h) illustrates sensitized adrenergic stimuli in BAT in Usf1/1 mice.

At thermoneutrality there is still decreased weight gain as a result of USF1 inactivation as evidenced in FIG. 16a. Furthermore, the lipid uptake by BAT is still increased at thermoneutrality in USF1 knockout mice (FIG. 16b). The observation that the major phenotypes of protection against weight gain and elevated triglyceride clearance persist at thermoneutrality, points to BAT being the driver of these phenotypes as result of USF1 inactivation.

As evidenced in FIGS. 16c-f, BAT is more sensitized to adrenergic stimuli, such as norepinephrine injection, secondary to USF1 inactivation. This is demonstrated by the greater rise in BAT temperature secondary to norepinephrine injection in Usf1 knockout mice, and by greater increase in oxygen consumption, again secondary to norepinephrine injection. These findings indicated that USF1 inactivation sensitizes BAT to adrenergic stimuli.

USF1 inactivation leads to increased BAT thermogenesis secondary to lipid administration. When injected intralipid solution into the mice, there is significant BAT temperature rise as compared to wild-type animals. These findings indicate that USF1 inactivation induces enhanced diet-induced thermogenesis. This finding is of particular importance since enhanced diet-induced thermogenesis has been implicated in protection against obesity.

The increased sensitivity of BAT resulting from USF1 inactivation is due to BAT specific rather than systemic effects of USF1. By silencing USF1 using shRNA in brown adipocyte cell line, we have demonstrated the higher sensitivity of these cells to norepinephrine. Both UCP1 expression (25-fold as compared to 5 fold in scrambled treated cells) and lipolysis were elevated in brown adipocytes silenced for USF1. These findings indicate that by targeting USF1 inhibition specifically to BAT, we can achieve elevated thermogenesis.

Accordingly, we suggest methods for treating and preventing conditions such as human metabolic syndrome, atherosclerosis, obesity, chronic vascular inflammation, and insulin resistance by inhibiting Usf-1 specifically in brown adipose tissue.

Example 11. Screening of USF1 Inhibition by Using Two Different Approaches

1) We apply the state-of-the art RNA interference technology in which the messenger RNA of USF1 is degraded, thereby reducing the intracellular protein levels of the gene. This approach is used in different types of cell cultures, such as fibroblasts and human hepatocytes. In order to follow the response of Usf-1 silencing Western blot analysis with monospecific antibodies against USF-1 are used or a specific USF-1 ELISA assay to measure Usf-1 on a protein level.

2) We apply a chemical library of approximately 75,000 compounds and establish a cell culture monitoring system where again fibroblasts or hepatocytes are used. To assess inhibition of the physiological function of USF1 as a transcription factor, we measure the expression of relevant target genes of USF1 such as apoA-V, apoA-I, and ABCA1.

Example 12. Silencing of USF-1 Function in Human Hepatocytes

The silencing of USF1 in human hepatoma cells (HuH7) will be performed using specific antisense oligonucleotides (ASO), siRNAs or chemical compounds in test. About 70% confluent Huh7 cells are transiently transfected for 48 hours with Interferin (Polyplus-transfection SA, Strasbourg, France) and 1 nM siRNA according to manufacturer's instructions. Chemical inhibitors with relevant concentration range will be added to cell culture medium and the response time will be first validated via measuring relative mRNA expression levels of the USF-1 target genes such as apoA-V, apoA-I, and ABCA1.

Example 13. Gene Expression Analysis from USF1 Silenced HuH7 Cells

RNA is extracted using the RNeasy Mini Kit (Qiagen) according to manufacturer's instructions. Quality of RNA is analyzed using the Bioanalyzer platform (Agilent Technologies). Two micrograms of total RNA are treated according to standard Affymetrix eukaryotic RNA labeling protocols (Affymetrix, Santa Clara, Calif.). Fifteen micrograms of biotin labeled cRNA is fragmented according to Affymetrix eukaryotic sample protocol. Hybridization, staining, and washing of the Affymetrix Mouse Genome 430 2.0 Arrays are performed using the Affymetrix Fluidics Station 450 and Hybridization Oven 640 under standard conditions. The raw data are processed using the GCRMA-normalization.

Example 14 Development of Usf-1-Inhibitors

A critical step in the identification of novel small molecular compounds usable in therapy is to generate a wide spectrum of molecules belonging to the previously identified active families. In case of USF1 (SEQ ID NO:7) this means that the protein domain for these compounds will be the USF1 specific amino acid region responsible for the binding to the promoter of the target genes. The availability of a large array of compounds is mandatory to successfully select the most potent, selective and effective, but also the least toxic ones with the most suitable pharmacokinetic and pharmacodynamics properties.

To test cell lines for use in testing whether small molecular compounds or ASOs can be used for USF1 inhibition, we have developed USF1 targeting siRNAs. Their sequences are: gacccaaccagtgtgtgcta (SEQ ID NO: 1), gattagaggtcgtcatcaa (SEQ ID NO: 2), and ggtgggattctatccaaag (SEQ ID NO:3). Using these siRNAs we have achieved 70-90% knockdown of USF1 mRNA. The silencing of USF1 was performed with in vitro with Human Hepatoma cells HuH7 with 70% confluence transfected for 48 h with 1 nM siRNA.

These siRNAs will be stored in nanoparticles to deliver them into appropriate target tissues. Brown adipose tissue is a preferred target tissue.

Small molecular size inhibitors will be screened in collaboration with Institute for Molecular Medicine Finland (FIMM). Small molecular library available includes approximately 75,000 compounds. Those molecules that are identified to inhibit USF1 in vitro, will be tested in animal model.

Example 15 Use of Nanoparticles in Targeting siRNAs or ASOs to BAT

Nanoparticles offer a promising medical tool for targeted drug (either small molecular chemical compound, siRNA or anti-sense-oligonucleotide, ASO) delivery to the target site and this approach is increasingly used to treat cancer and atherosclerosis. This is also a promising tool to use these nanoparticles as cargo vehicles for targeted delivery of anti-USF1 agents to cells expressing USF1 protein including brown adipose tissue. For high diagnostic and therapeutic efficacy, these nanoparticles should have the ability to identify the targets at the cell membrane initially at endothelial cell layer or specifically on brown adipose tissue and these include cell membrane proteins such as integrins, adhesion molecules, and receptors. Therefore, the surfaces of nanoparticles have to be decorated with the targeting moieties including antibodies, proteins, peptide, or other ligands.

Since there are several types of nanoparticles available their nature/characteristics (physical, chemical), size, toxicity/pathogenicity, biodegradability, coating (effect of coating alone or coating+core) of particles should be defined and described in detail to interpret the results optimally in case of inhibiting USF1.

We will pack the USF1 inhibitors inside proper nanoparticles and test their functionality in i) human hepatocyte cultures ii) brown adipose cell cultures, iii) in a mouse model, and finally iv) in humans.

Our study is a compelling example how the promises of hypothesis-free genetic studies in humans being able to generate novel, previously unpredicted biological information, can transform into reality. In the knockout mice, we have recapitulated the dyslipidemic phenotype USF1 variants were originally associated with in Finnish FCHL families. Furthermore, we have identified Usf1 to be a powerful metabolic master regulator, able to integrate adiposity with plasma lipoprotein metabolism through the control of brown adipose tissue activity. The most essential discovery in our study is the extraordinary array of beneficial metabolic phenotypes conferred by Usf1 deficiency. The protection against obesity, insulin resistance, fatty liver, and atherosclerosis induced by Usf1 deficiency signifies that the potential of USF1 as a therapeutic target cannot be ignored.

The therapeutic applications according to this invention include inhibiting or silencing USF1. Molecules and compounds capable of inhibiting or silencing the gene are beneficial and useful for treating atherosclerosis, and obesity, protection against fatty liver, improving sensitivity to insulin, improving fat profile in individual's blood and activating brown fat tissue.

The therapeutically active compounds may be administered to a patient in need thereof subcutaneously, or orally. Other ways of administering are also possible. In case of inhibiting nucleic acid sequence (e.g. antisense oligonucleotide (ASO) or siRNA approach), a construct comprising desired promoter sequences and the inhibiting nucleic acid sequence may be administered as a vaccine.

Material and Methods
Animals

We use a congenic strain in C57BL/RCC background in our studies with littermate controls. In the notation N=X/Y presented in figure legends, X represents the number of Usf1 +/+ mice and Y represents the number of Usf1 −/− mice throughout this disclosure unless otherwise specified. All animal procedures were reviewed and approved by the local animal care committee and local government authorities. The high fat diet used in this study contains 21.2% fat, 48.5% carbohydrate, 17.3% protein, and 0.2% cholesterol by weight (Harlan TD.88137, Madison, Wis.).

Generation of Usf1 Knockout Mice

Usf1 deficient mouse embryonic stem cells were acquired from German Genetrap Consortium (clone M121B03)[14]. The retrovirally delivered vector ROSAbetageo+2 was inserted into the 4$^{th}$ exon of Usf1. The integration site was confirmed by sequencing both ends of the inserted construct. M121B03 cells were then injected into C57BL/6J blastocysts in Biocenter Oulu transgene unit (Oulu, Finland). Heterozygous Usf1 mice were crossed and genotyped by PCR. The wild type allele generated a 167 bp fragment with the primers 5'-GGCGCAGTGGTACTGGAGAGGA-3' (forward)(SEQ ID NO:4) and 5'-ACCCCAAACCCCAG-GCGGCA-3' (SEQ ID NO:5) and the knockout allele a 457 bp fragment with the same forward primer and the reverse primer 5'-TGACGCGCCGCTGTAAAGTGTTA-3'. (SEQ ID NO:6) Illumina Mouse medium density panel (1449 markers) was used to select the heterozygous male having the highest degree of allelic homozygosity with the C57BL/RCC strain. Congeneity was achieved after backcrossing for 5 generations. These congenic animals were used in all experiments unless otherwise stated. For atherosclerosis studies, the congenic Usf1 +/− mice were bred with Ldlr −/− mice[15] (The Jackson Laboratory, Bar Harbor, Me.) to generate animals with genotypes of Usf1 −/− Ldlr −/− and Usf1 +/+ Ldlr −/−.

Measurement of Plasma Lipid Levels and HDL Particle Lipid Composition

Blood was drawn after the mice were fasted for a 4-h period, mice were mildly sedated using fentanyl 52.5 µg/kg and fluanisone 1.65 mg/kg (Hypnorm@), and serum was obtained by a standard low-speed centrifugation and stored at −80° C. before analysis. Total cholesterol (CHOD-PAP 1489232 kit; Roche Diagnostics GmbH, Mannheim, Germany), choline-containing phospholipids (990-54009; Wako Chemicals GmbH, Neuss, Germany and/or Diagnostic Systems, Holzheim, Germany) and triglycerides (GPO-PAP 1488872 kit; Roche Diagnostics GmbH) were measured using fully enzymatic methods. Mouse apoA-I was analyzed using ELISA method as described[16].

Analysis of Lipoprotein Profiles

Serum lipoprotein profile analysis was performed by fast-performance liquid chromatography (FPLC; Merck-HPLC System) using Superose 6 HR 10/30 size-exclusion chromatography column (GE Healthcare, Buckinghamshire, UK). The column was first equilibrated with 10 mM Na-phosphate buffer, pH 7.4 containing 140 mM NaCl, and then 100-150 µl of serum was applied to the column with a flow rate of 0.5 ml/min. Fractions (0.5 ml) were collected, and analyzed for cholesterol, triglycerides, and phospholipids.

Isolation and Composition of Mouse HDL

HDL was isolated from pooled mice serum samples by sequential ultracentrifugation using Table-Top ultracentrifuge (Beckmann Optima TL, USA) and KBr for density adjustment (Havel et al. 1955). Serum sample pool (1.0 mL) was first adjusted to the density (d) of 1.019 g/mL and the centrifuge tube filled with a d=01.019 g/mL KBr solution to the total volume of 3 mL. The samples were centrifuged at +5 C for 2 hrs at the speed 100 000 rpm (corresponding relative centrifugal field 500 000×g). After centrifugation very low and intermediate density lipoproteins (VLDL+ IDL) were recovered in the top 1 mL fraction and the bottom was adjusted to the density of 1.063 g/mL using solid KBr, filled to 3 mL with d=1.063 g/mL KBr solution and centrifuged (+5 C, 3 hrs, 100 000 rpm). The top 1 mL fraction contained low density lipoproteins (LDL). To get the total mouse HDL fraction the LDL bottom fraction was adjusted with solid KBr to the density of 1.21 g/mL, the vials filled with KBr 1.21 g/mL density solution and then centrifuged (+5 C, 18 hrs, 100 000 rpm). Total HDL was obtained in top 1 mL fraction. The isolated HDL was dialyzed against phosphate-buffered saline (PBS, pH 7.4) and stored at +4 C before analysis. Isolated HDL was analyzed for lipids and apoA-I using the methods described above.

Silencing of USF1 in THP-1 Macrophages

The human monocytic cell line, THP-1, was cultured in RPMI medium supplemented with 10% fetal bovine serum and penicillin/streptomycin and 25 mM HEPES. For transduction, 20000 cells were seeded on 24-well plates and treated for 24 h with SIGMA MISSION lentiviral preparations containing either the control shRNA expression vector (MISSION® pLKO.1-puro Non-Target shRNA) or the Usf1 silencing shRNA expression vector (233475) at a MOI of ~1. Cells were selected with 6 ug/ml of puromycin for 14 days and were then used for cholesterol efflux assay experiments.

Cholesterol Efflux from THP-1 Macrophages

THP-1 human monocytes (ATCC, Manassas, Va.) were grown at 37° C. in suspension culture in RPMI 1640 medium supplemented with 10% FBS, 25 mM Hepes, and 1% penicillin/streptomycin until differentiation into macrophages by the addition of 100 nM phorbol myristate acetate (PMA, Sigma). Differentiated THP-1 macrophages were loaded with 25 μg/ml acetylated LDL labeled with [$^3$H] cholesterol for 48 h. The cells were then washed with PBS, and 2% serum or HDL (as determined by 25 μg/mL HDL protein) derived from either Usf1 −/− or +/+ mice were added as cholesterol acceptors. After 24 h incubation, the growth medium was collected and radioactivity was determined by liquid scintillation counting. The cell layer was washed with PBS, followed by addition of 0.2 M NaOH and further incubated for 24 h at +4 C, after which the radioactivity was assessed. Wells incubated without added acceptors were used as controls. Cholesterol efflux is presented as dpm in medium divided by the cell protein content (dpm/μg cell protein).

Post-Heparin Lipase Activities

Mice were mildly sedated using Fentanyl 52.5 μg/kg and Fluanisone 1.65 mg/kg (Hypnorm®). An intravenous injection of heparin (LEO Pharma®, Ballerup, Denmark) was given to the mice (150 IU/kg body weight), and after 15 minutes, blood samples were drawn from the saphenous vein. Post-heparin LPL activity was measured as previously described[26]. Briefly, [Carboxyl-$^{14}$C]-Triolein (S.A. 2.2 GBq/mmol, PerkinElmer) and glyceryl trioleate (Sigma) emulsified with gum arabic was used as a substrate. Post-heparin samples (15-25 μL) were incubated with the substrate and human serum (as source for apoC-II, LPL cofactor) for 1 hour at 37° C. Radioactivity of the liberated fatty acids was measured by liquid scintillation counting (Wallac LS β-Counter, Turku, Finland). LPL activity is expressed as μmol FFA/mL/h.

In Vivo Hepatic VLDL Secretion

Mice were fasted for 12 h and then anesthetized by i.p. administration of midazolam (12.5 mg/kg). Triton WR-1339 (Sigma), which blocks lipolysis and hepatic VLDL uptake, was dissolved in 0.9% NaCl and subsequently injected via tail-vein (500 mg/kg of Triton WR-1339). Blood samples were drawn from the saphenous vein before and 30 min, 60 min, and 90 min after Triton WR-1339 administration. Plasma triglyceride levels were measured from the samples as described above. The mice were fed a standard chow diet and were of 12-15 weeks of age. Serum volumes of the mice (mL) were assumed to be 0.04706 mL/g multiplied by mouse weight (g).

Plasma Hormone Measurements

The serum hormone levels were measured using Rat Thyroid Hormone Panel Kit (T4, T3), Mouse Adipocyte Magnetic Bead Panel (leptin, resistin, TNF-a, Mcp-1), Mouse Adiponectin Magnetic Bead Single Plex Kit (adiponectin), and Mouse Pituitary Magnetic Bead Panel (TSH) kits (Merck Millipore, Billerica, Mass.) as quantified on a BioPlex (Bio-Rad, Hercules, Calif.).

Turnover Studies

VLDL-like triglyceride rich emulsion particles were prepared as previously described[17]. For turnover studies, mice were sedated using Fentanyl and Fluanisone (Hypnorm®). Mice were injected via the tail-vein with 200 μL of emulsion particles corresponding to 1.0 mg of triglyceride. After 15 minutes, the animals were perfused with PBS, organs were harvested and weighed. The organs were dissolved overnight at 65° C. tissue solubilizer (Soluene®, Perkin-Elmer, 1 mL per organ sample). Lipid uptake was calculated as percentage of the injected dose dpm/mg tissue.

To inhibit LPL function, tetrahydrolipstatin (12.5 mg/mL of tetrahydrolipstatin in DMSO) was diluted to 1.25 mg/mL in 10% DMSO in PBS. This solution was injected into mice before administration of VLDL-like emulsion particles as described above. Again, mice were sacrificed after 15 min of injection. The tetrahydrolipstatin solution was a courtesy of Dr. Alexander Bartell and Dr. Jörg Heeren.

Intestinal Absorption of Free Fatty Acids and Triglycerides

Mice were fasted overnight (12 h). For the intestinal absorption experiment, mice were gavaged with 100 μL virgin olive oil (Il Genio, Tuscany, Italy) per mouse containing 5 μCi 3H Triolein [9,10-3H(N)] (SIGMA) and 1 μCi of 14C Oleic acid [1-14C] (SIGMA). Blood samples were drawn before gavage (t=0) and at 45 min and 90 min after gavage, and serum $^3$H and $^{14}$C radioactivity was determined. Plasma volumes (ml) were calculated as 0.04706×body weight (g). The intestinal tract (i.e., duodenum, proximal jejunum, distal jejunum, and ileum) was isolated and washed twice with 4 mM cholic acid in PBS. Both the intestinal tissue and the non-absorbed luminal content were examined for $^3$H and $^{14}$C radioactivity to determine the amount of absorbed versus non-absorbed olive oil present in the intestinal tract. The small intestine was divided into sections as follows; duodenum:jejunum:ileum 1:3:2, and jejunum further to proximal and distal jejunum 1:1.

Quantification and Compositional Analysis of Aortic Atherosclerosis

To induce atherosclerosis, 12-week old male mice (Usf1−/−Ldlr−/− and Usf1+/+Ldlr−/−) were fed a high-fat diet (Harlan TD.88137, Madison, Wis.) for 20 weeks after which the mice were analyzed for the development of atherosclerotic lesions. At sacrifice the arterial tree was transcardially perfused with PBS. The heart and the whole aorta were dissected out, and the aorta was fixed in 10% neutral-buffered formalin for a minimum of 48 h before preparation. After careful removal of the adventitia under a preparation microscope, the dissected aorta was pinned to wax plates and stained with Sudan IV (Sigma-Aldrich, St. Louis, Mo.). The lesion area (expressed as percent) was obtained by dividing the Sudan IV positive area by the area of the aortic arch and descending aorta, respectively. The heart including the aortic root was frozen in OCT embedding medium (Sakura Finetek Europe B.V., The Netherlands). The light contrast was equally adjusted in both representative images.

Cryosections (10 µm) of the aortic sinus were cut throughout the aortic root starting at the origin of the root and ending at the point at which the valve leaflets were no longer visible. Every $10^{th}$ section, corresponding to sections every 100 µm, was used for a particular staining. This resulted in 5 sections for each staining, and covered a 400 µm segment of the ascending aorta. All evaluated sections were routinely stained with Mayer's hematoxylin (Sigma). Neutral lipids and collagen were visualized with Oil-Red-O (Sigma) and Masson Trichrome Stains (Sigma), respectively. Immunohistochemical staining were performed with antibodies against a macrophage-specific antigen (MOMA-2, monoclonal rat anti-mouse IgG2b, 0.5 mg/ml, diluted 1:800, Serotec), alpha-smooth muscle cell actin (A 5228, monoclonal mouse IgG2a, 2 mg/ml, diluted 1:1000, Sigma). In each staining, a negative isotype control was included. The rat primary antibodies were detected with ImmPRESS anti-rat Ig (mouse adsorbed) Reagent kit (Vector Laboratories) and the mouse primary antibody was detected with ARK kit (Dako). NovaRED (Vector Laboratories) was used as a substrate for the peroxidase-conjugated secondary antibodies. Tissue sections were viewed with a Nikon Eclipse E600 microscope (Nikon Co., Tokyo, Japan) and photographed with a digital camera (Spot RT color operated with Spot advanced software, version 4.1, Diagnostic Instruments, Sterling Heights, Mich., USA). Areas positive for MOMA-2, α-smooth muscle actin, and collagen were determined by computer-assisted image quantification (Image-Pro Plus software, Media Cybernetics). The cell numbers and the color-positive areas were determined and expressed as percentages of the total lesion areas. To correct for any variation in aortic size, each lesion area was related to the cross-sectional aortic area circumscribed by the internal elastic lamina, which, again, was calculated from the length of the respective internal elastic lamina. The analyses were carried out in a blinded fashion.

Magnetic Resonance Imaging Analysis

Animals were anesthetized using fentanyl 0.395 mg/kg, fluanisone 12.5 mg/kg, (Hypnorm®) and midazolam 6.25 mg/kg (Dormicum®). Total body fat was assessed by magnetic resonance imaging (MRI). MRI measurements were performed with a 4.7 T MR Scanner (PharmaScan, Bruker, Ettlingen, Germany). The coil was a dedicated rat head coil (Bruker linear birdcage coil, maximum gradient amplitude 300 mT/s, rise time<80 µs). After a scout, fast spin echo [rapid acquisition with relaxation enhancement (RARE)] sequence was used with and without chemical shift selective fat suppression. TR/TEeff=3723/36 ms, rare factor=8, matrix size=256×256, field-of-view=40×40 mm, 34 slices, slice thickness=1 mm. The MRI images were analyzed using Bruker ParaVision image analysis package by manually circling total area, visceral adipose tissue area, and subcutaneous adipose tissue area on each slice. In both male and female mice, the most cranial slice included in the analysis was the uppermost slice with both kidneys visible. The most caudal slice included in the analysis was the one with longest visible segment of the sigmoid colon in males and the bifurcation of the uterine horns in females. The anatomical boundaries were consistent between each animal.

Histology and Cell-Size Measurement

After 20 weeks of HFD feeding, gonadal white adipose tissue was isolated from Usf1 +/+(n=17) and Usf1 −/− (n=12) mice, fixed overnight in 10% formalin, dehydrated, and embedded in paraffin for sectioning. Sections were stained with hematoxylin and eosin. Computer-assisted image quantification of adipocyte size was manually carried out using the Image-Pro Plus software (Media Cybernetics, Warrendale, Pa.). The average adipocyte size was calculated by quantifying the areas of 100 adipocytes from each mouse. The neutral lipid content of liver was studied by Oil Red O staining from frozen sections and the nuclei were briefly stained with hematoxylin. The histological analyses from brown adipose tissue were performed using standard hematoxylin and eosin staining.

Electron Microscopy Measurements

Electron microscopy measurements of BAT samples were performed on males on a chow diet for twelve months. The lipid droplets were measured in two ways. The average lipid droplet size was calculated from a representative area with >60 lipid droplets. Every undivided lipid droplet was included. The brown adipose tissue lipid content was calculated by dividing the lipid droplet covering area by the total area of the representative spot in the specimen. The quantification of lipid droplets was performed using Image-Pro Plus software.

Metabolic Studies

Metabolic rate of the mice was measured using a Comprehensive Laboratory Animal Monitoring System (CLAMS), an indirect open circuit calorimeter (Columbus Instruments, Columbus, Ohio). Mice were acclimated in metabolic chambers for 24 hours before analysis. Food and water were available ad libitum during the whole experiment. Mice were housed in center feeder cages, which allow food intake measurements with Oxymax/CLAMS center feeder (Columbus Instruments). Physical activity of the mice was monitored with Oxymax/CLAMS activity monitoring (Columbus Instruments). The movements (other than scratching, grooming, digging etc.) of each animal were determined by infrared beams in x and z axes. VCO2 and VO2 levels were measured for 2 days in 20° C. and on the $3^{rd}$ day mice were challenged with an 8-h cold tolerance period at 4° C. starting at 9 AM. Dark (8 PM-8 AM), light (8 AM-8 PM), and cold (10 AM-5 PM) conditions were used for the calculation of physical activity, VO2, and VCO2. The experiments were conducted at room temperature (+20° C.) and thermoneutral conditions (+30° C.).

Insulin Tolerance Test

Insulin tolerance test was performed by insulin injection (1 IU/kg, Actrapid®, Novo Nordisk) into peritoneal cavity after the mice were fasted for 6 h. We took blood samples before (0 min) and 15, 30, 60, 90, and 120 min after insulin injection to measure glucose levels. Blood glucose concentration was measured from the tail tip using glucose meter, Contour®. Insulin tolerance test was conducted under mild sedation using fentanyl 52.5 µg/kg and fluanisone 1.65 mg/kg (Hypnorm®).

Hyperinsulinemic Euglycemic Clamp Analysis

Overnight fasted (16 h, starting at 5 PM), male Usf1 −/− and Usf +/+ mice were anaesthetized with 6.25 mg/kg Acepromazine (Alfasan, Woerden, The Netherlands), 6.25 mg/kg Midazolam (Roche, Mijdrecht, The Netherlands), and 0.31 mg/kg Fentanyl (Janssen-Cilag, Tilburg, The Netherlands). First, basal rates of glucose turnover were determined by administration of a primed continuous intravenous (i.v.) infusion of D-[1-$^{14}$C]glucose (0.3 µCi/kg/min; Amersham, Little Chalfont, UK) for 60 minutes. Subsequently, insulin (Actrapid, Novo Nordisk, Denmark) was administered i.v. by primed (4.1 mU), continuous (6.8 mU/h) infusion to attain steady-state hyperinsulinemia together with D-[1-$^{14}$C]glucose (0.3 µCi/kg/min; Amersham, Little Chalfont, UK) for 90 min. A variable i.v. infusion of a 12.5% D-glucose solution was used to maintain euglycemia as determined at 10-min intervals via tail bleeding (<3 µl, Accu-chek, Sensor Comfort; Roche Diagnostics, Mannheim, Germany). In the last 20 min of both experiments, blood samples were taken with intervals of 10 min. The glucose specific activities measured at 10 min intervals indicated the presence of steady-state conditions in all mice (data not shown). Hematocrit levels were similar in the basal and the hyperinsulinemic period for Usf1 −/− and Usf1 +/+ mice, indicating that the mice were not anemic. Subsequently, the mice were sacrificed and after perfusion with ice-cold PBS, organs were harvested and snap-frozen in liquid nitrogen.

Measurement of Hepatic Triglyceride Contents

Upon necropsy, sections of liver tissue were excised, snap-frozen in liquid nitrogen and stored at −70° C. Cellular lipids were extracted from the tissue by the method of Folch et. al.[18] and triglycerides were measured as glycerol after chloroform-methanol extraction and hydrolysis. Briefly, liver tissue (approximately 100 mg) was homogenized and sonicated in 1 mL 95% methanol and mixed with 2 mL chloroform. The organic phase was washed with 0.9% NaCl solution and dried under nitrogen. The residuals were dissolved in 200 µL of tetraethylammoniumhydroxide (diluted 1:28 with 95% ethanol) and incubated at 60° C. for 30 min with 200 µL of 0.05 M HCl. Triglycerides are hydrolyzed and glycerol released during the incubation with tetraethylammoniumhydroxide. The formed glycerol was measured enzymatically as described above for serum samples.

Lipid Analysis of Feces

Mice were individually housed for 4 days to determine food intake and collect feces quantitatively both after a 6-week and 20-week periods of HFD feeding. Feces were weighed, freeze-dried, and ground. Fecal secretion of triglycerides and fatty acids was determined in feces, collected during 24 h time period using enzymatic methods. Briefly, carefully dried feces samples were extracted for lipids by the method of Bligh and Dyer[19] and triglycerides were measured after chloroform-methanol extraction. After extraction, triglycerides were phase-separated into chloroform and after evaporation of chloroform the dried lipid residue was solubilized in glass vials to 400 µL of PBS-5% Triton X-100 and incubated for 30 min at 95 C with occasional mixing. Solubilized mixture was transferred to Eppendorff-tubes and residual, non-soluble material removed by centrifugation (3000 rpm, 1 min). Triglycerides and free fatty acids were then analyzed enzymatically as described above for serum samples. Triglycerides and free fatty acids were also analyzed from the water phase. The data are expressed as µmol TG or FFA per mg dried feces.

Blood Pressure Measurements

Systolic blood pressure of the mice was measured using a validated volume-pressure recording tail-cuff system (CODA non-invasive blood pressure system, Kent Scientific Corp., Torrington, Conn., USA; 3×10 measured cycles)[20].

Statistical Analysis

Statistical analyses were performed using SPSS and R. Experimental results are shown as the mean±s.e.m. Analyses were performed using Student's T test. Significance threshold was set at p<0.05.

REFERENCES

1. Gregor, P. D., Sawadogo, M. & Roeder, R. G. The adenovirus major late transcription factor USF is a member of the helix-loop-helix group of regulatory proteins and binds to DNA as a dimer. Genes Dev. 4, 1730-1740 (1990).
2. Sawadogo, M. & Roeder, R. G. Interaction of a gene-specific transcription factor with the adenovirus major late promoter upstream of the TATA box region. Cell 43, 165-75 (1985).
3. Roy, A. L., Meisterernst, M., Pognonec, P. & Roeder, R. G. Cooperative interaction of an initiator-binding transcription initiation factor and the helix-loop-helix activator USF. Nature 354, 245-8 (1991).
4. Pajukanta, P. et al. Linkage of familial combined hyperlipidaemia to chromosome 1q21-q23. Nat Genet 18, 369-73 (1998).
5. Pajukanta, P. et al. Familial combined hyperlipidemia is associated with upstream transcription factor 1 (USF1). Nature genetics 36, 371-6 (2004).
6. Kristiansson, K. et al. Association analysis of allelic variants of USF1 in coronary atherosclerosis. Arteriosclerosis, thrombosis, and vascular biology 28, 983-9 (2008).
7. Laurila, P. P. et al. Genetic association and interaction analysis of USF1 and APOA5 on lipid levels and atherosclerosis. Arteriosclerosis, thrombosis, and vascular biology 30, 346-52 (2010).
8. Komulainen, K. et al. Risk alleles of USF1 gene predict cardiovascular disease of women in two prospective studies. PLoS genetics 2, e69 (2006).
9. Auro, K. et al. USF1 gene variants contribute to metabolic traits in men in a longitudinal 32-year follow-up study. Diabetologia 51, 464-72 (2008).
10. Laurila, P. P. et al. Genomic, transcriptomic, and lipidomic profiling highlights the role of inflammation in individuals with low high-density lipoprotein cholesterol. Arterioscler. Thromb. Vasc. Biol. 33, 847-857 (2013).
11. Fournier, N. et al. Role of HDL phospholipid in efflux of cell cholesterol to whole serum: studies with human apoA-I transgenic rats. J. Lipid Res. 37, 1704-1711 (1996).
12. Putt, W. et al. Variation in USF1 shows haplotype effects, gene:gene and gene:environment associations with glucose and lipid parameters in the European Atherosclerosis Research Study II. Hum Mol Genet 13, 1587-97 (2004).
13. Bartell, A. et al. Brown adipose tissue activity controls triglyceride clearance. Nat Med 17, 200-5 (2011).
14. Hansen, J. et al. A large-scale, gene-driven mutagenesis approach for the functional analysis of the mouse genome. Proceedings of the National Academy of Sciences of the United States of America 100, 9918-22 (2003).
15. Ishibashi, S. et al. Hypercholesterolemia in low density lipoprotein receptor knockout mice and its reversal by adenovirus-mediated gene delivery. J. Clin. Invest. 92, 883-893 (1993).
16. van Haperen, R. et al. Human plasma phospholipid transfer protein increases the antiatherogenic potential of high density lipoproteins in transgenic mice. Arterioscler. Thromb. Vasc. Biol. 20, 1082-1088 (2000).
17. Redgrave, T. G. & Maranhao, R. C. Metabolism of protein-free lipid emulsion models of chylomicrons in rats. Biochim. Biophys. Acta 835, 104-112 (1985).
18. Folch, J., Lees, M. & Sloane Stanley, G. H. A simple method for the isolation and purification of total lipids from animal tissues. J Biol Chem 226, 497-509 (1957).

19. BLIGH, E. G. & DYER, W. J. A rapid method of total lipid extraction and purification. *Can. J. Biochem. Physiol.* 37, 911-917 (1959).

20. Feng, M. et al. Validation of volume-pressure recording tail-cuff blood pressure measurements. *Am J Hypertens* 21, 1288-91 (2008).

What is claimed is:

1. A method to increase triglyceride, fatty acid and glucose uptake by mammalian brown adipose tissue cells, said method comprising inhibiting USF1 encoding gene in brown adipose tissue cells by introducing a siRNA or an antisense oligonucleotide (ASO) in the brown adipose tissue cells, wherein the siRNA or the antisense oligonucleotide (ASO) inhibits expression of said USF1 encoding gene in the brown adipose tissue.

2. The method of claim 1, wherein the mammalian cells are human cells.

3. The method of claim 1, wherein the siRNA is according to SEQ ID NO:1 or SEQ ID NO:2.

4. A method to treat one or more conditions selected from the group consisting of atherosclerosis, obesity, fatty liver, decreased sensitivity to insulin in a subject having such condition, wherein the method comprises a step of activating brown adipose tissue of the subject by inhibiting or silencing expression of Usf1-gene in brown adipose tissue cells of the subject, by introducing into the brown adipose tissue a siRNA molecule or an antisense oligonucleotide (ASO) that inhibits or silences expression of said Usf-1 gene in the brown adipose tissue.

5. The method of claim 4, wherein the expression of Usf1-gene is inhibited or silenced by administering to the subject a pharmaceutically effective amount of a molecule having an inhibitory or silencing effect on the expression of the gene and causing deficiency of USF1 protein in whole body or in targeted brown adipose tissue, wherein the molecule having an inhibitory or silencing effect is a siRNA molecule or antisense oligonucleotide (ASO) that inhibits or silences expression of said Usf1-gene in brown adipose tissue of the subject.

6. The method of claim 5, wherein the molecule has an inhibitory effect and it is administered subcutaneously or orally.

7. The method of claim 5, wherein the molecule is packed in a nanoparticle.

8. The method of claim 5, wherein the siRNA is according to SEQ ID NO:1 or SEQ ID NO:2.

9. The method of claim 5, wherein the molecule is provided in a vector and administered as a vaccine.

10. A method to activate brown adipose tissue in a mammal, said method comprising a step of inhibiting or silencing Usf-1 gene in the brown adipose tissue of the mammal by introducing a siRNA or an antisense oligonucleotide in the brown adipose tissue cells, wherein the siRNA or the antisense oligonucleotide (ASO) inhibits said Usf-1 gene in the brown adipose tissue cells.

* * * * *

```
                        SEQUENCE LISTING

<160> NUMBER OF SEQ ID NOS: 7

<210> SEQ ID NO 1
<211> LENGTH: 22
<212> TYPE: DNA
<213> ORGANISM: Artificial sequence
<220> FEATURE:
<223> OTHER INFORMATION: chemically synthesized
<220> FEATURE:
<221> NAME/KEY: misc_feature
<222> LOCATION: (1)..(22)
<223> OTHER INFORMATION: forward primer

<400> SEQUENCE: 1
ggcgcagtgg tactggagag ga                                            22

<210> SEQ ID NO 2
<211> LENGTH: 20
<212> TYPE: DNA
<213> ORGANISM: artificial sequence
<220> FEATURE:
<223> OTHER INFORMATION: Chemically synthesized
<220> FEATURE:
<221> NAME/KEY: misc_feature
<222> LOCATION: (1)..(20)
<223> OTHER INFORMATION: primer

<400> SEQUENCE: 2
accccaaacc ccaggcggca                                               20

<210> SEQ ID NO 3
<211> LENGTH: 23
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(23)
<223> OTHER INFORMATION: reverse primer

<400> SEQUENCE: 3
tgacgcgccg ctgtaaagtg tta                                           23

<210> SEQ ID NO 4
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<222> LOCATION: (1)..(19)
<223> OTHER INFORMATION: siRNA

<400> SEQUENCE: 4
gacccaacca gtgtggcta                                                19

<210> SEQ ID NO 5
<211> LENGTH: 19
<212> TYPE: DNA
<213> ORGANISM: artificial sequence
<220> FEATURE:
<223> OTHER INFORMATION: chemcially synthesized
<220> FEATURE:
```

```
<221> NAME/KEY: misc_feature
<222> LOCATION: (1)..(19)
<223> OTHER INFORMATION: siRNA

<400> SEQUENCE: 5
gattagaggt cgtcatcaa                                                  19

<210> SEQ ID NO 6
<211> LENGTH: 19
<212> TYPE: DNA
<213> ORGANISM: artificial sequence
<220> FEATURE:
<223> OTHER INFORMATION: chemically synthesized
<220> FEATURE:
<221> NAME/KEY: misc_feature
<223> OTHER INFORMATION: siRNA

<400> SEQUENCE: 6
ggtgggattc tatccaaag                                                  19

<210> SEQ ID NO 7
<211> LENGTH: 310
<212> TYPE: PRT
<213> ORGANISM: Homo sapines
<220> FEATURE:
<221> NAME/KEY: PEPTIDE
<222> LOCATION: (1)..(310)
<223> OTHER INFORMATION: USF-1

<400> SEQUENCE: 7

Met Lys Gly Gln Gln Lys Thr Ala Glu Thr Glu Glu Gly Thr Val Gln
1               5                   10                  15

Ile Gln Glu Gly Ala Val Ala Thr Gly Glu Asp Pro Thr Ser Val Ala
            20                  25                  30

Ile Ala Ser Ile Gln Ser Ala Ala Thr Phe Pro Asp Pro Asn Val Lys
        35                  40                  45

Tyr Val Phe Arg Thr Glu Asn Gly Gly Gln Val Met Tyr Arg Val Ile
    50                  55                  60

Gln Val Ser Glu Gly Gln Leu Asp Gly Gln Thr Glu Gly Thr Gly Ala
65                  70                  75                  80

Ile Ser Gly Tyr Pro Ala Thr Gln Ser Met Thr Gln Ala Val Ile Gln
                85                  90                  95

Gly Ala Phe Thr Ser Asp Asp Ala Val Asp Thr Glu Gly Thr Ala Ala
            100                 105                 110

Glu Thr His Tyr Thr Tyr Phe Pro Ser Thr Ala Val Gly Asp Gly Ala
        115                 120                 125

Gly Gly Thr Thr Ser Gly Ser Thr Ala Ala Val Val Thr Thr Gln Gly
    130                 135                 140

Ser Glu Ala Leu Leu Gly Gln Ala Thr Pro Pro Gly Thr Gly Gln Phe
145                 150                 155                 160

Phe Val Met Met Ser Pro Gln Glu Val Leu Gln Gly Gly Ser Gln Arg
                165                 170                 175

Ser Ile Ala Pro Arg Thr His Pro Tyr Ser Pro Lys Ser Glu Ala Pro
            180                 185                 190

Arg Thr Thr Arg Asp Glu Lys Arg Arg Ala Gln His Asn Glu Val Glu
        195                 200                 205

Arg Arg Arg Arg Asp Lys Ile Asn Asn Trp Ile Val Gln Leu Ser Lys
    210                 215                 220

Ile Ile Pro Asp Cys Ser Met Glu Ser Thr Lys Ser Gly Gln Ser Lys
225                 230                 235                 240
```

```
Gly Gly Ile Leu Ser Lys Ala Cys Asp Tyr Ile Gln Glu Leu Arg Gln
            245                 250                 255

Ser Asn His Arg Leu Ser Glu Glu Leu Gln Gly Leu Asp Gln Leu Gln
            260                 265                 270

Leu Asp Asn Asp Val Leu Arg Gln Gln Val Glu Asp Leu Lys Asn Lys
            275                 280                 285

Asn Leu Leu Leu Arg Ala Gln Leu Arg His His Gly Leu Glu Val Val
        290                 295             300

Ile Lys Asn Asp Ser Asn
305             310
```